(12) United States Patent  
Rowland et al.

(10) Patent No.: US 8,062,209 B2  
(45) Date of Patent: Nov. 22, 2011

(54) IMPLANTABLE PUMP

(75) Inventors: Randall P. Rowland, Eden Prairie, MN (US); Gary A. Rocheleau, Maple Grove, MN (US); Charles C. Kuyava, Eden Prairie, MN (US); Randy L. Morningstar, Brooklyn Park, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 12/967,776

(22) Filed: Dec. 14, 2010

(65) Prior Publication Data

US 2011/0087068 A1   Apr. 14, 2011

Related U.S. Application Data

(60) Continuation of application No. 11/186,225, filed on Jul. 21, 2005, now Pat. No. 7,874,978, which is a division of application No. 10/725,711, filed on Dec. 2, 2003, now Pat. No. 6,991,601.

(60) Provisional application No. 60/430,200, filed on Dec. 2, 2002.

(51) Int. Cl.  
   *A61F 5/00*   (2006.01)

(52) U.S. Cl. .......................................... 600/40

(58) Field of Classification Search .............. 600/29–32, 600/38–41; 128/DIG. 25, 843; 623/11.11; 473/300–303  
See application file for complete search history.

(56) References Cited

U.S. PATENT DOCUMENTS

| | | | |
|---|---|---|---|
| 988,120 | A | 3/1911 | Lott |
| 1,863,057 | A | 3/1930 | Innes |
| 3,312,215 | A | 4/1967 | Silber |
| 3,344,791 | A | 10/1967 | Foderick |
| 3,397,699 | A | 8/1968 | Kohl |
| 3,503,400 | A | 3/1970 | Osthagen et al. |
| 3,642,004 | A | 2/1972 | Osthagen et al. |
| 3,731,670 | A | 5/1973 | Loe |
| 3,797,478 | A | 3/1974 | Walsh et al. |
| 3,812,841 | A | 5/1974 | Isaacson |
| 3,954,102 | A | 5/1976 | Buuck |
| 4,222,377 | A | 9/1980 | Burton |
| 4,224,934 | A | 9/1980 | Scott et al. |
| 4,235,227 | A | 11/1980 | Yamanaka |
| 4,244,370 | A | 1/1981 | Furlow et al. |
| 4,267,829 | A | 5/1981 | Burton et al. |
| 4,344,434 | A | 8/1982 | Robertson |
| 4,369,771 | A * | 1/1983 | Trick .............................. 600/40 |

(Continued)

FOREIGN PATENT DOCUMENTS

DE   25 37 506 A1   3/1977

(Continued)

OTHER PUBLICATIONS

Gregory, John G. et al., The Inflatable Penile Prosthesis: Failure of the Rear Tip Extender in Reducing the Incidence of Cylinder Leakage, The Journal of Urology, vol. 131, pp. 668-669 (Apr. 1984).

(Continued)

*Primary Examiner* — John Lacyk  
(74) *Attorney, Agent, or Firm* — Kimberly K. Baxter; Gregory L. Koeller

(57) ABSTRACT

An implantable pump with a plurality of protrusions and grooves is described.

3 Claims, 39 Drawing Sheets

U.S. PATENT DOCUMENTS

| | | |
|---|---|---|
| 4,383,525 A | 5/1983 | Scott et al. |
| 4,392,562 A | 7/1983 | Burton et al. |
| 4,407,278 A | 10/1983 | Burton et al. |
| 4,412,530 A | 11/1983 | Burton |
| 4,453,536 A | 6/1984 | Abild |
| 4,489,732 A | 12/1984 | Hasson |
| 4,537,183 A | 8/1985 | Fogarty |
| 4,553,959 A | 11/1985 | Hickey et al. |
| 4,559,931 A | 12/1985 | Fischell |
| 4,566,446 A * | 1/1986 | Fogarty ............................ 600/40 |
| 4,566,466 A | 1/1986 | Ripple et al. |
| 4,571,241 A | 2/1986 | Christopher |
| 4,572,168 A | 2/1986 | Fischell |
| 4,590,927 A | 5/1986 | Porter et al. |
| 4,594,998 A | 6/1986 | Porter et al. |
| 4,596,242 A | 6/1986 | Fischell |
| 4,628,912 A | 12/1986 | Fischell |
| 4,632,435 A | 12/1986 | Polyak |
| 4,651,721 A | 3/1987 | Mikulich et al. |
| 4,653,485 A | 3/1987 | Fishell |
| 4,669,456 A | 6/1987 | Masters |
| 4,671,261 A | 6/1987 | Fischell |
| 4,682,583 A | 7/1987 | Burton et al. |
| 4,710,169 A | 12/1987 | Christopher |
| 4,718,410 A | 1/1988 | Hakky |
| 4,730,607 A | 3/1988 | Fischell |
| 4,782,826 A | 11/1988 | Fogarty |
| 4,807,608 A | 2/1989 | Levius |
| 4,850,963 A | 7/1989 | Sparks et al. |
| 4,890,866 A | 1/1990 | Arp |
| 4,895,139 A | 1/1990 | Hauschild et al. |
| 4,932,938 A | 6/1990 | Goldberg et al. |
| 4,941,461 A | 7/1990 | Fischell |
| 4,944,732 A | 7/1990 | Russo |
| 4,958,630 A | 9/1990 | Rosenbluth et al. |
| 4,960,425 A | 10/1990 | Yan et al. |
| 4,968,294 A | 11/1990 | Salama |
| 5,010,882 A | 4/1991 | Polyak et al. |
| 5,022,942 A | 6/1991 | Yan et al. |
| 5,030,199 A | 7/1991 | Barwick et al. |
| 5,033,893 A | 7/1991 | Hainaut |
| 5,034,009 A | 7/1991 | Mouchel |
| 5,041,092 A | 8/1991 | Barwick |
| 5,048,510 A | 9/1991 | Hauschild et al. |
| 5,048,511 A | 9/1991 | Rosenbluth et al. |
| 5,062,417 A | 11/1991 | Cowen |
| 5,063,914 A | 11/1991 | Cowen |
| 5,067,485 A | 11/1991 | Cowen |
| 5,074,849 A | 12/1991 | Sachse |
| 5,085,650 A | 2/1992 | Giglio |
| 5,088,980 A | 2/1992 | Leighton |
| 5,090,424 A | 2/1992 | Simon et al. |
| 5,112,295 A | 5/1992 | Zinner et al. |
| 5,114,398 A | 5/1992 | Trick et al. |
| 5,131,906 A | 7/1992 | Chen |
| 5,141,509 A * | 8/1992 | Burton et al. ................... 600/40 |
| 5,167,611 A | 12/1992 | Cowan |
| 5,171,272 A | 12/1992 | Levius |
| 5,186,180 A | 2/1993 | Bellas |
| 5,250,020 A | 10/1993 | Bley |
| 5,263,981 A | 11/1993 | Polyak et al. |
| 5,295,978 A | 3/1994 | Fan et al. |
| 5,329,834 A | 7/1994 | Wong |
| 5,344,388 A | 9/1994 | Maxwell et al. |
| 5,468,213 A | 11/1995 | Polyak |
| 5,484,450 A | 1/1996 | Mohamed |
| 5,512,033 A | 4/1996 | Westrum, Jr. et al. |
| 5,553,379 A | 9/1996 | Westrum, Jr. et al. |
| 5,645,924 A | 7/1997 | Hamilton |
| 5,658,280 A | 8/1997 | Issa |
| 5,702,387 A | 12/1997 | Arts et al. |
| 5,704,895 A | 1/1998 | Scott et al. |
| 5,736,251 A | 4/1998 | Pinchuk |
| 5,804,318 A | 9/1998 | Pinchuk et al. |
| 5,810,764 A | 9/1998 | Eggers et al. |
| 5,851,176 A | 12/1998 | Willard |
| 5,887,630 A | 3/1999 | Shipley |
| 5,895,424 A | 4/1999 | Steele, Sr. et al. |
| 5,925,069 A | 7/1999 | Graves et al. |
| 6,171,233 B1 | 1/2001 | Willard |
| 6,346,492 B1 | 2/2002 | Koyfman |
| 6,443,887 B1 | 9/2002 | Derus et al. |
| 6,533,719 B2 | 3/2003 | Kuyava et al. |
| 6,558,315 B1 | 5/2003 | Kuyava |
| 6,723,042 B2 | 4/2004 | Almli et al. |
| 6,991,601 B2 | 1/2006 | Kuyava et al. |
| 7,874,978 B2 | 1/2011 | Kuyava et al. |
| 2002/0082473 A1 | 6/2002 | Henkel et al. |

FOREIGN PATENT DOCUMENTS

| | | |
|---|---|---|
| EP | 0397 500 A2 | 11/1990 |
| WO | WO 92/03107 A | 3/1992 |

OTHER PUBLICATIONS

Hellstrom, WJG, Three-Piece INFLATABL4E Penile Prosthesis Components (Surgical Pearls on Reservoirs, Pumps, and Rear-Tip Extenders), Int'l J of Impotence Research, vol. 15. Suppl 5, pp. S136-138 (2003).

Joseph, David et al., Bilateral Dislocation of Rear Tip Extenders From the Inflatable Penile Prosthesis, The Journal of Urology, vol. 1128, pp. 1317-1318 (Dec. 1982).

Kim, Sae-Chul, M.D., Mechanical Reliability of AMS Hydraulic Penile Prostheses, Journal of Korean Medical Science, vol. 10. No. 6, pp. 422-425 (Dec. 1995).

Levine, Laurence A. et al., Mechanical Reliability and Safety of, and Patient Satisfaction With the Ambicor Inflatable Penile Prosthesis: Results of a 2 Center Study, The Journal of Urology, vol. 166, pp. 932-937 (Sep. 2001).

Malloy, Terrance R. et al., Improved Mechanical Survival With Revised Model Inflatable Penile Prosthesis Using Rear-Tip Extenders, The Journal of Urology, vol. 128, pp. 489-491 (Sep. 1982).

Montague, Drogo K., Experience With Semirigid Rod and Inflatable Penile Prosthesis, The Journal of Urology, vol. 129, pp. 967-968 (May 1983).

Mooreville, Michael et al., Implantation of Inflatable Penile Prosthesis in Patients With Severe Corporeal Fibrosis: Introduction of a New Penile Cavernotome, The Journal of Urology, vol. 162, pp. 2054-2057 (Dec. 1999).

Mulcahy, John J., Distal Corporplasty for Lateral Extrusion of Penile Cylinders, The Journal of Urology, vol. 161, pp. 193-195 (Jan. 1999).

Parulkar, B.G. et al., Revision Surgery for Penile Implants, Int. J. Impotence Res., vol. 6, pp. 17-23 (1994).

Randrup, Eduardo R., M.D., Penile Implant Surgery: Rear Tip Extender That Stays BE3HIND, Urology, vol. XXXIX, No. 1, pp. 667-669 (Jan. 1992).

Stein, Avi et al., Malleable Penile Prosthesis Removal Leaving Behind the Rear Tip Extenders: A Clinical Presentation, Urol. Intl, 50, pp. 119-120 (1993).

AMS 700.TM. Inflatable Penile Prosthesis Product Line, Inservice Script brochure, American Medical Systems (1992).

Ultrex/Ultrex Plus brochure, American Medical Systems, Inc. (1998).

Description of Ultrex Fabric and Yarns (Mar. 30, 2001).

Mentor Alpha.RTM. Inflatable Penile Prosthesis, Surgical Protocol, 15 pages (1998).

Mentor Urology Products, 20 pages (May 1998).

Mentor Alpha.RTM., The Results Are In, 14 pages (Apr. 1997).

Mentor Alpha.RTM.Narrow Base, Simplifying Penile Implant Surgery by Making Difficult Cases More Manageable, 2 pages (Oct. 1996).

Mentor.RTM. Acu-Form.RTM. Penile Prosthesis, 2 pages (Aug. 1997).

Mentor.RTM. Acu-Form.RTM. Penile Prosthesis, Malleable Penile Prosthesis, Surgical Protocol, 8 pages (Sep. 1997).

* cited by examiner

IMPLANTABLE PUMP

REFERENCE TO RELATED APPLICATIONS

This application claims the benefit of, and is a continuation of, pending U.S. application Ser. No. 11/186,225, filed Jul. 21, 2005, which is a divisional application of U.S. Pat. No. 6,991,601, filed Dec. 2, 2003, which claims priority to U.S. Provisional Patent Application No. 60/430,200, filed Dec. 2, 2002. Each of the identified applications is hereby incorporated by reference into the present application.

BACKGROUND

This invention generally relates to an implantable pump assembly for inflating a prosthesis. More particularly, the invention relates to a pump assembly for an inflatable penile prosthesis.

One common treatment for male erectile dysfunction is the implantation of a penile prosthesis. Such a prosthesis typically includes a pair of inflatable cylinders which are fluidly connected to a fluid (typically liquid) reservoir via a pump and valve assembly. The two cylinders are normally implanted into the corpus cavernosae of the patient and, in some embodiments, a reservoir may be implanted in the patient's abdomen. The pump assembly is implanted in the scrotum. During use, the patient actuates the pump and fluid is transferred from the reservoir through the pump and into the cylinders. This results in the inflation of the cylinders and thereby produces the desired penis rigidity for a normal erection. Then, when the patient desires to deflate the cylinders, a valve assembly within the pump is actuated in a manner such that the fluid in the cylinders is released back into the reservoir. This deflation then returns the penis to a flaccid state.

U.S. Pat. No. 4,566,466 discloses an implantable penile prosthesis comprising a fluid reservoir, a pump and elongate cylindrical prosthetic members. The pump includes an exterior surface with a plurality of circular ridges. The ridges are separated by grooves and extend around the exterior surface of the pump in a continuous, uninterrupted fashion. The device is operated by grasping the scrotal sac and squeezing the pumping section of the pump through the scrotal sac wall. The ridges of the pumping section are said to prevent the pumping section from slipping off the user's grasp during pumping. However, there is no structure blocking movement of tissue relative to the pump along a longitudinal axis of a groove.

U.S. Pat. No. 5,141,509 discloses an inflatable penile prosthesis. The prosthesis has an inflatable cylinder, a fluid reservoir, pump means and valves.

U.S. Pat. No. 4,437,457 discloses an improved pressure control valve for a medical device. U.S. Pat. No. 4,682,583 discloses an artificial sphincter. The sphincter includes a pump, a housing and a node.

U.S. Pat. Nos. 4,537,183, 5,851,176 and 5,167,611 disclose penile prostheses with a pump and a plurality of circular ridges.

The Alpha I® Inflatable Penile Prosthesis was sold in the United States more than a year prior to the filing date of the present application by Mentor of Santa Barbara, Calif. The Alpha I Prosthesis included a pump assembly with a pump housing with release bars and a pump with a plurality of ridges that were separated by grooves that extended around the exterior surface of the pump in a continuous, uninterrupted fashion. To return the prosthesis to a flaccid state, the user was instructed to feel the protruding release bars and then squeeze them.

The continuous nature of the grooves and ridges is believed to present a problem. There is no structure to block movement of tissue along a direction substantially parallel to a longitudinal axis of a groove.

The ridges of the Alpha prosthesis are relatively thin and are spaced close together. Grooves between the ridges provide very little room for tissue to extrude into. This is undesirable as squeezing tissue into the grooves is believed to help anchor the pump to the tissue during the act of squeezing. FIG. 1A depicts ribs of a prior art Alpha device. One ridge was measured with an average width of about 0.024 inches and a depth of about 0.029 inches. The grooves tend to be somewhat small. One groove was measured with an average width of about 0.034 inches. FIG. 1A shows an area 1' between ribs 2' of a prior art Alpha prosthesis pump. This area was measured as 0.0012 square inches. There is very little area between the ribs 2'. This small area is not optimal for affording tissue to extrude between the ribs when the patients squeezes tissue to compress the pump bulb The outer surfaces of the ridges of the Alpha I prosthesis tend to be rounded, with a large radius at the top. One radius was measured at 0.012 inches. This is also believed to be a problem as the rounded tips do not afford optimal tissue purchase and can result in tissue sliding off the tip of the ridge.

The Mark II® Inflatable Penile Prosthesis was sold in the United States more than a year prior to the filing date of the present application by Mentor of Santa Barbara, Calif. This device included a pump assembly including a resipump and a release ring.

The Mark II prosthesis has a single squeeze pump. The size of the pump limits the pressure that can be transmitted to the cylinders and therefore limits the stiffness of the cylinder. The Mark II cylinder is believed to afford a much less stiff cylinder than the Alpha I cylinder.

The release ring of the Mark II includes a plurality of ribs. Again, these ribs are rounded and slippery.

SUMMARY OF THE INVENTION

In one aspect, the present invention includes an improved protrusion and groove system for an implantable pump. The protrusion and groove system affords space for tissue to extrude into and surfaces to block movement of the implant relative to tissue in three mutually perpendicular directions. In preferred embodiments, the protrusions are discontinuous and have edges that block movement in a direction substantially parallel to a longitudinal axis of the grooves. Also preferably, the protrusions have less rounded tips than prior art ribs to afford greater tissue purchase and a firmer grasp of the implantable pump.

In one aspect, the present invention comprises a pump assembly for an implantable prosthesis. The pump assembly comprises a housing including a valve assembly, and a pump bulb that is squeezable through tissue. The pump bulb has a plurality of discrete, discontinuous, spaced apart protrusions. The protrusions are sized, shaped and arranged to resist relative movement between tissue and the implantable prosthesis when the pump bulb is squeezed. The protrusions comprise shaped structures selected from the group consisting of oval, linear, elliptical, circular, polygonal, triangular and combinations thereof.

In another aspect, the pump assembly comprises a housing including a valve assembly, and a pump bulb having a plurality of protrusions with a longitudinal axes. The protrusions are arranged to be spaced apart by a plurality of grooves with longitudinal axes. The protrusions have ends that separate the protrusions from each other. The ends preferably form channels having longitudinal axes extending at angles relative to the longitudinal axes of the grooves. In one embodiment, the angles are approximately ninety degrees. The protrusions have tip portions and the distance between tip portions of adjacent protrusions is preferably greater than 0.05 inches. The tip portions have rounds and the rounds preferably have a radius of less than about 0.012 inches. More preferably, the rounds have a radius of less than about 0.006 inches.

In one embodiment, the ends of the protrusions form a channel with a longitudinal axis that is configured at an angle relative to the longitudinal axes of the protrusions. In one embodiment, the angle is approximately ninety degrees. In another, it is approximately, forty-five degrees.

In another aspect, the present invention comprises a pump assembly for a prosthesis that is implantable in tissue. The pump assembly comprises a housing including a valve assembly, a pump bulb having a plurality of protrusions spaced apart by grooves, wherein the protrusions and grooves have structure capable of blocking movement of the prosthesis relative to the tissue in three dimensions.

In yet another aspect, the present invention comprises an implantable penile prosthesis. The device comprises a reservoir for storing fluid; a pump assembly in fluid communication with the reservoir; and a pair of cylinders in fluid communication with the pump assembly. The pump assembly comprises a housing including a valve assembly. The housing is adapted to be deformed to operate the valve assembly. The housing has at least three protrusions, and a pump bulb.

In another aspect, the present invention comprises an implantable penile prosthesis comprising a reservoir for storing fluid; a pump assembly in fluid communication with the reservoir; and a pair of cylinders in fluid communication with the pump assembly. The pump assembly comprises a pump bulb; a bar shaped housing including a valve assembly. The housing is adapted to be deformed to operate the valve assembly. The housing has end portions and side portions. Each end portion has at least one protrusion. The side portions have a side bar.

DETAILED DESCRIPTION OF PREFERRED EMBODIMENTS

Figure 1:
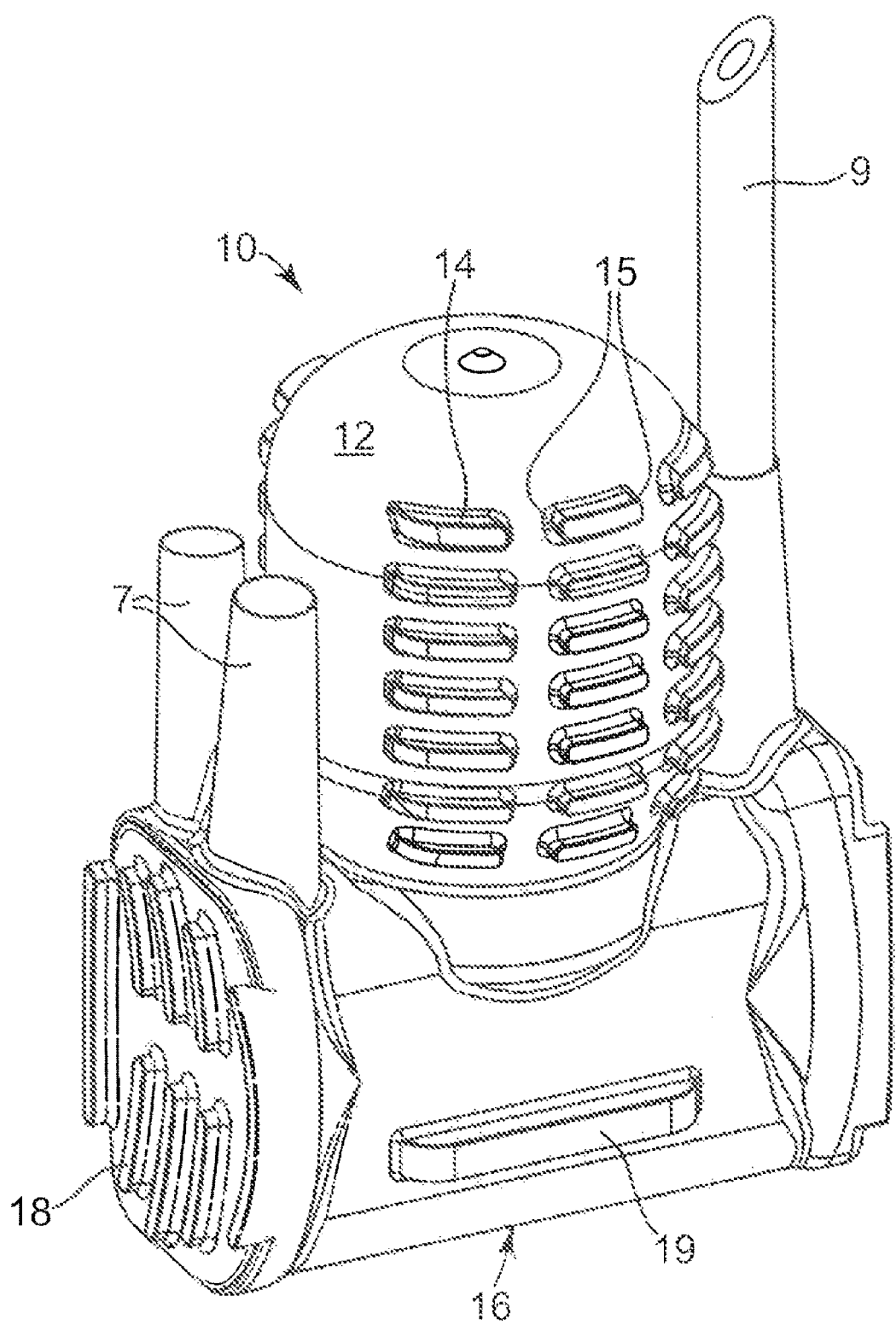
FIG. 1 is a perspective view of an embodiment of pump assembly according to one aspect of the present invention.
Figure 1A:
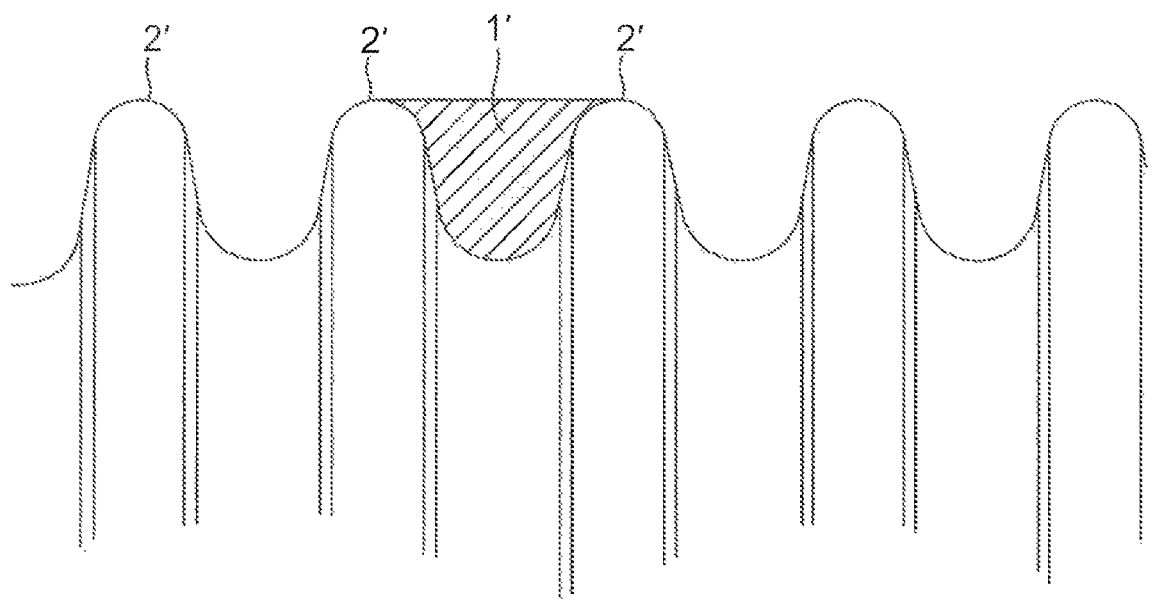
FIG. 1A is a schematic depiction of a portion of a prior art pump for a penile prosthesis.
Figure 2:
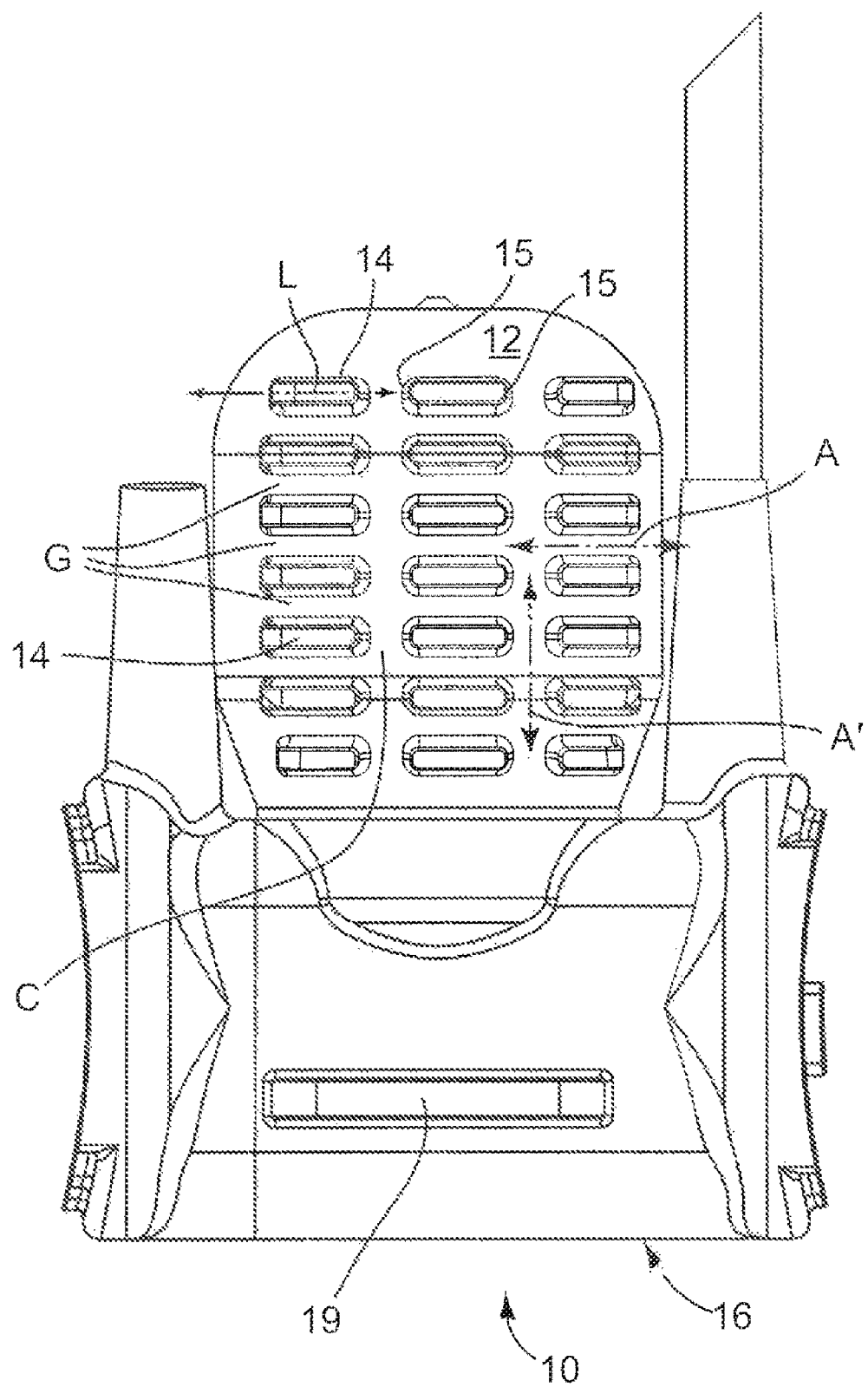
FIG. 2 is a side view of the pump assembly of FIG. 1.
Figure 3:
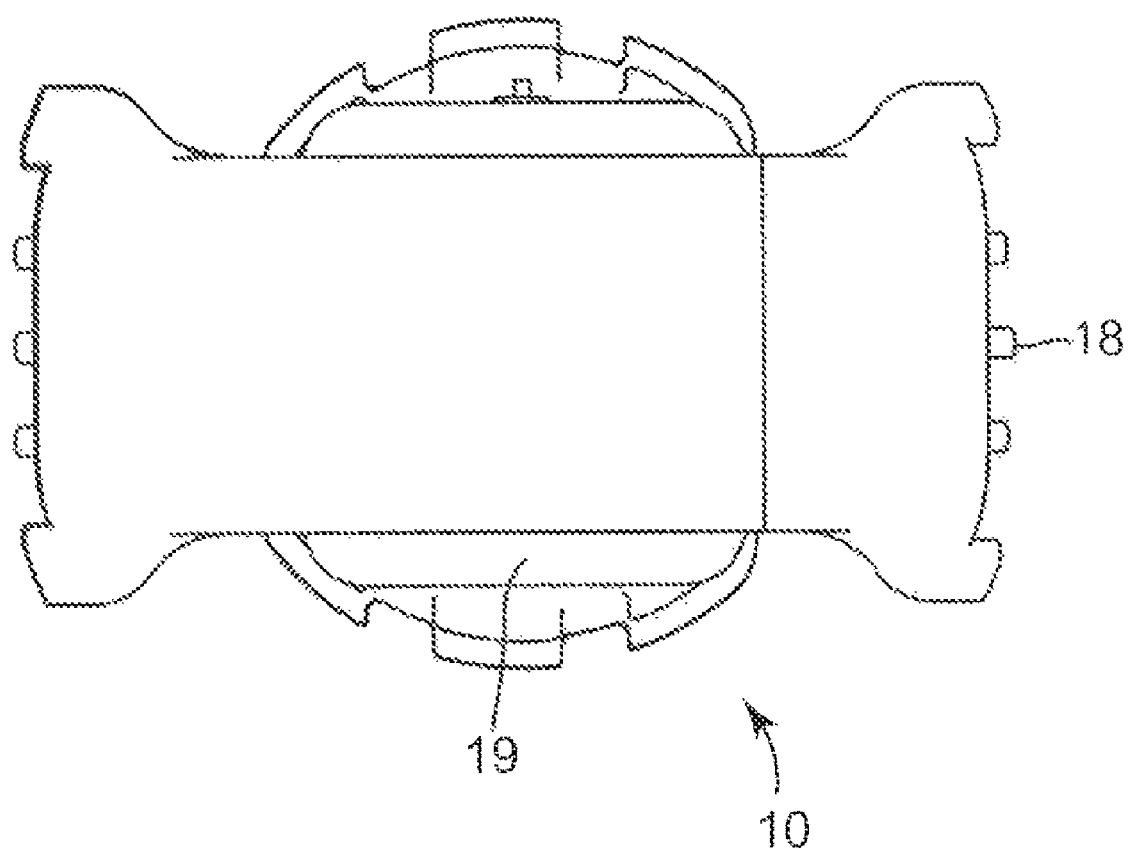
FIG. 3 is a bottom view of the pump assembly of FIG. 1.

Referring to FIGS. 1 through 6, there is shown an embodiment of pump assembly 10 according to an aspect of the present invention. The pump assembly 10 includes a pump bulb 12 having a plurality of protrusions 14 with a longitudinal axes L (FIG. 2). The protrusions 12 are spaced apart by a plurality of grooves G with longitudinal axes A. Preferably, the protrusions 14 have ends 15 that separate the protrusions 14 from each other.

The pump assembly 10 is adapted to be in fluid communication with a reservoir via tube 9. The pump assembly 10 is adapted to be in fluid communication with implantable inflatable members via tubes 7.

The protrusion ends 15 form channels C having longitudinal axes A' extending at angles relative to the longitudinal axes A of the grooves G. Preferably the angle is approximately ninety degrees, but other angles are also contemplated herein. Also preferably, the ends 15 face each other across channels C.

The protrusions 14 facilitate traction on the pump bulb 12 and resist movement of the bulb 12 relative to tissue in multiple directions as force is applied to compress bulb 12. Preferably the protrusions 15 resist slipping latitudinally as well as longitudinally.

The protrusions, grooves, and channels are sized shaped and arranged to afford efficient interaction with tissue. Preferably, the protrusions help direct the application of force to desired areas, afford tactile location and fixation within tissue (e.g. of the scrotum). A variety of factors affect protrusion performance, including the material comprising the protrusions, their width, their height, and shape including cross sectional shape. In general, the protrusions should be robust enough to hold the pump assembly substantially stationary relative to tissue during operation of an implant associated with the pump assembly 10. The protrusions 14 should be sufficiently flexible to avoid unduly irritating tissue.

As an example, not intended to be limiting, the protrusion may comprise shaped structures selected from the group consisting of oval, linear, elliptical, circular, polygonal, triangular and combinations thereof.

The pump bulb 12 is preferably is squeezable through tissue (e.g. scrotal tissue or other tissue). Preferably, the protrusions 14 are sized, shaped and arranged to resist relative movement between tissue and the implantable prosthesis when the pump bulb 12 is squeezed. Also preferably, the protrusions 14 and grooves G have structure capable of blocking movement of the implantable prosthesis relative to tissue in three mutually perpendicular directions.

Figure 11:
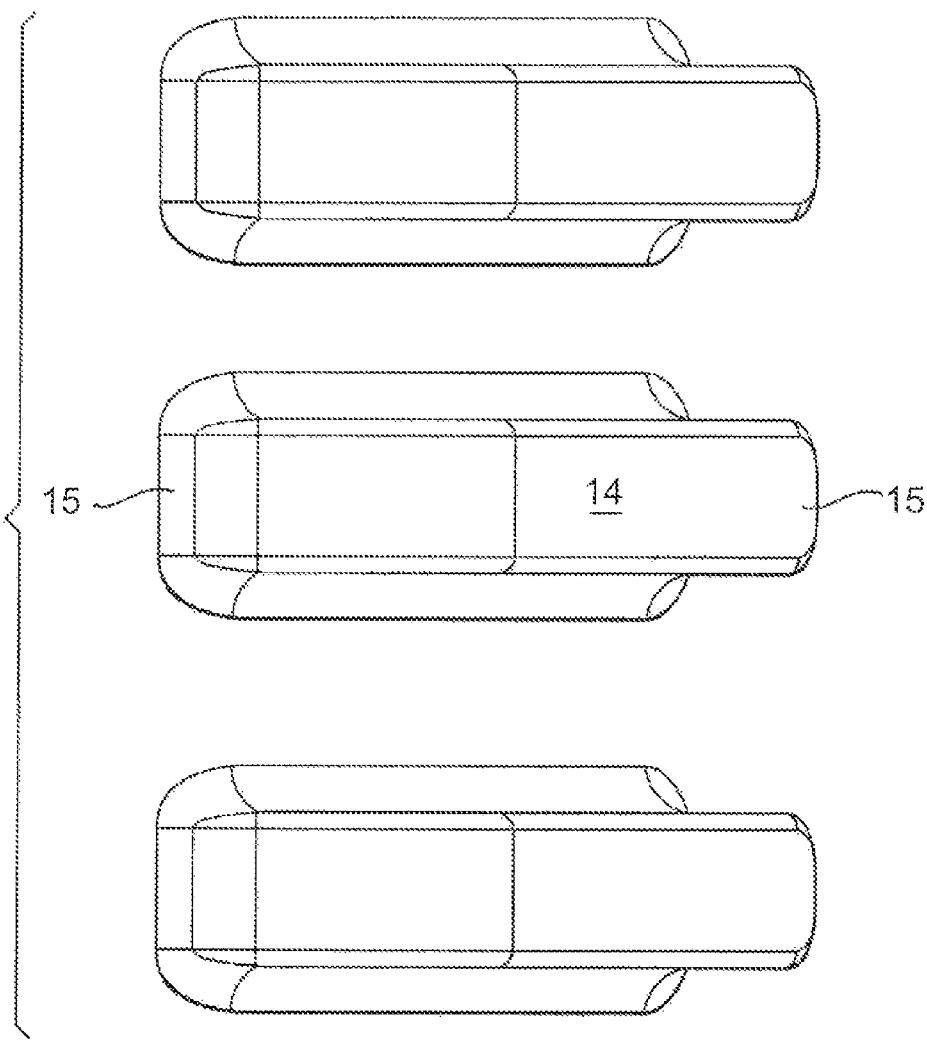
FIG. 11 is an enlarged view of some of the protrusions shown in FIG. 2.
Figure 27:
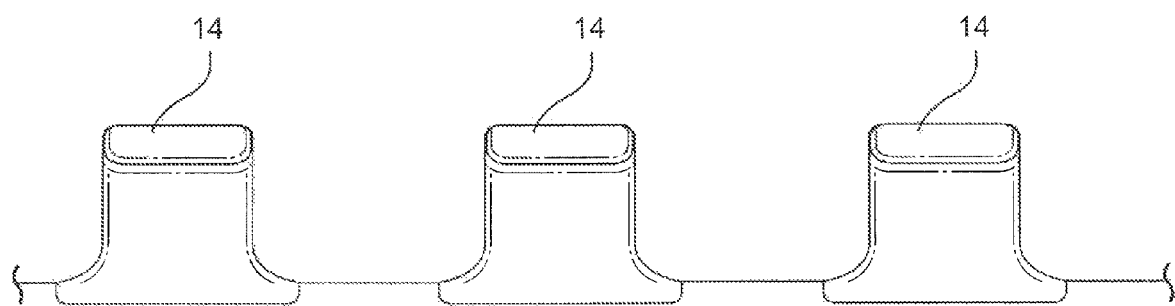
FIG. 27 is an side view of the protrusions of FIG. 11.

Referring now to FIGS. 11 and 27, there is shown an embodiment of protrusion 14 according to a preferred aspect of the present invention. In a preferred embodiment, the protrusions are constructed from 50-55 durometer silicone elastomer, available from Nusil of California. Any suitable medical grade materials may be utilized, such as, but no limited to silicone rubber (e.g. polydimethyl siloxane), thermoset materials, Thermoset or thermoplastic urethanes, C-flex, santoprene thermoplastics and the like.

Figure 25B:
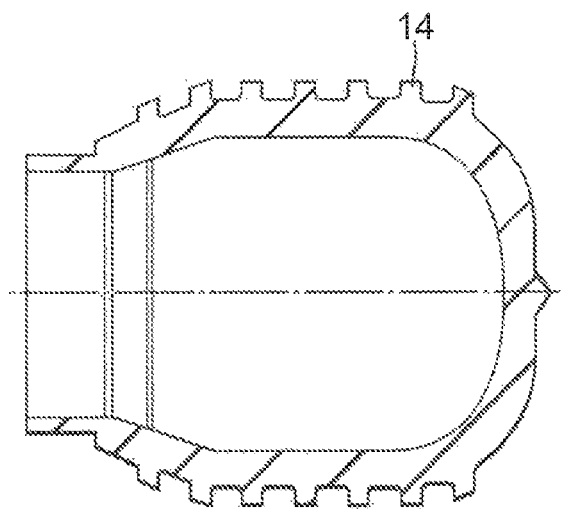
FIG. 25B is a sectional view of the pump bulb of FIG. 25A.
Figure 25A:
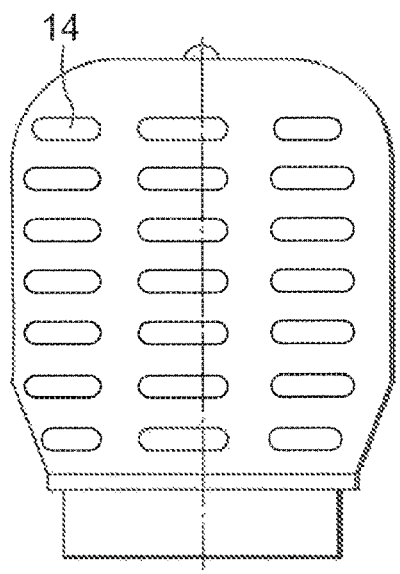
FIG. 25A is a side view of a pump bulb according to a preferred embodiment of the present invention.
Figure 25:
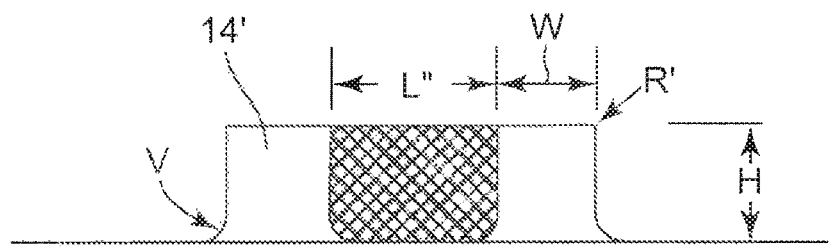
FIG. 25 is a sketch of a cross-sectional view of protrusions according to an embodiment of the present invention.

Referring now to FIG. 25, there is shown another sketch of a protrusion and groove assembly according to the present invention. In one embodiment, the protrusions 14' have a width W at the tip of about 0.04 inches, a height H of about 0.04 inches, and the tip edges have a radius R' of about 0.005 inches. The groove has a length L" between tips of about 0.065 inches with a valley radius V of about 0.015 inches. FIGS. 25A and 25B are engineering drawings of a preferred embodiment of the protrusions, with preferred dimensions shown in inches.

The radius R' of the tips of the protrusions 14 is preferably small (e.g. less than 0.012 inches), more preferably they are less than about 0.006 inches. When the user squeezes the pump bulb, it is believed that forces in tissue are concentrated at or near the edges of the tips of the protrusions. This is believed to assist in providing stability for the pump assembly 10. However, the radius should not be so small as to damage or unduly irritate tissue.

The pump assembly also includes a housing 16 that includes a valve assembly. In general, some portion of the housing 16 is deflectable or deformed to actuate the valve assembly. The valve assembly may comprise any suitable valve assembly including, but not limited to, those valve assemblies disclosed in U.S. Provisional Application Nos. 60/453,684, filed Mar. 10, 2003, 60/508,123 filed Oct. 2, 2003; 60/507,973, filed Oct. 2, 2003, and 60/507,975, filed Oct. 2, 2003; published U.S. Pat. Application Nos. 2002-91302-A1, 2002-82709-A1; 2002-82708-A1; 2002-82473-A1; and 2002-82471-A1; and U.S. Pat. Nos. 6,443,887 and 6,533,719. Various components useable in conjunction with the present invention are also disclosed in the previously mentioned applications and U.S. Provisional Application Nos. 60/507,972 and 60/507,974 which were filed Oct. 2, 2003.

The valve assembly may also comprise the valve assemblies associated with the Mark II Inflatable Penile Prosthesis and the Alpha I Inflatable Penile Prosthesis, each available from Mentor Corp. Examples of valve assemblies are also disclosed in U.S. Pat. Nos. 4,566,466 and 4,537,183.

Figure 7:
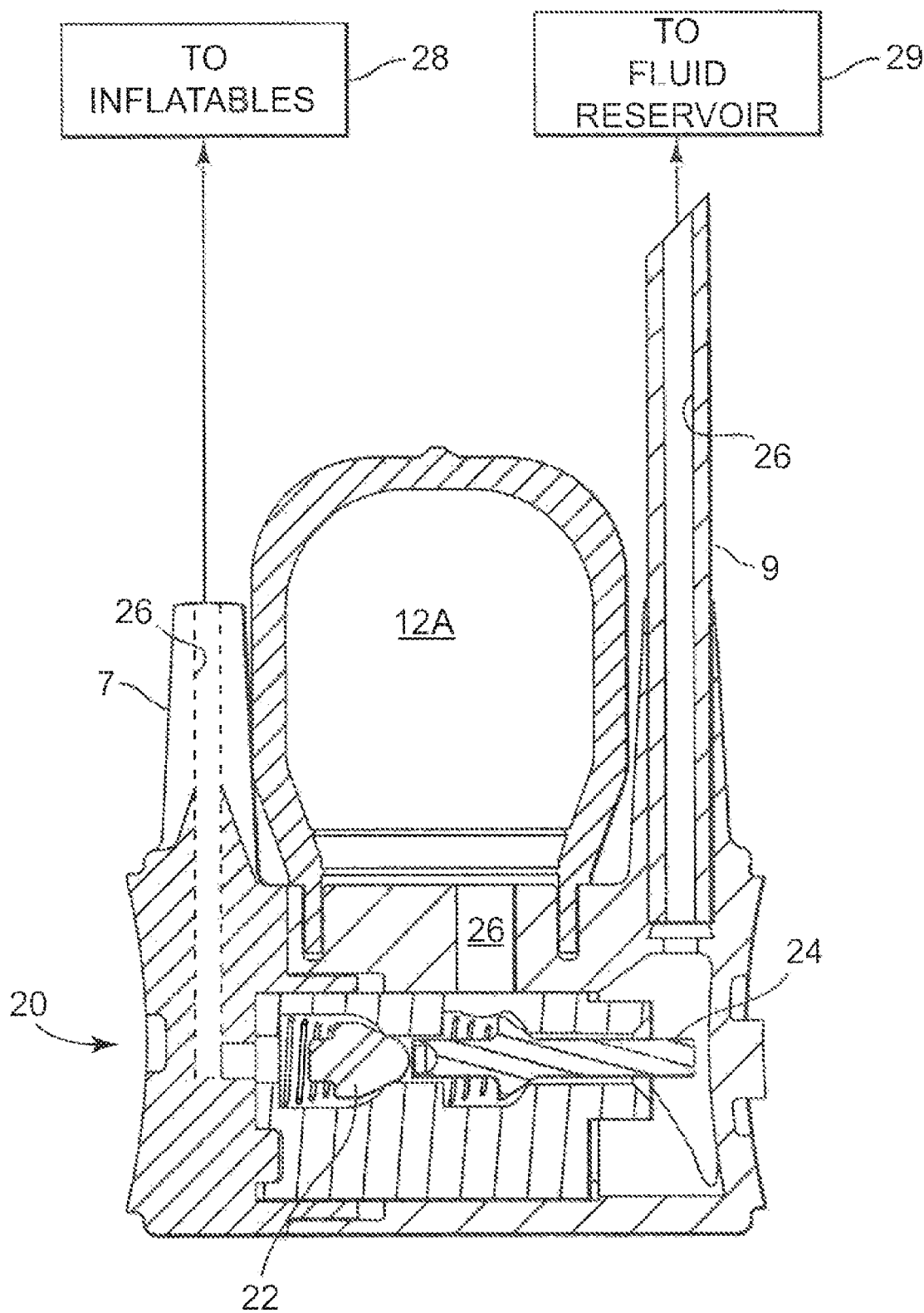
FIG. 7 is a sectional view of one embodiment of valve assembly for use with the present invention, taken approximately along lines A-A of FIG. 6.

Referring now to FIG. 7, there is shown an embodiment of valve assembly 20. This example of valve assembly includes a spring biased poppet or ball valve 22, a spring biased suction poppet 24 and fluid passageways 26 for communicating with a pump bulb 12A, inflatables 28 (e.g. penile prosthesis cylinders) and a fluid reservoir 29.

Figure 8:
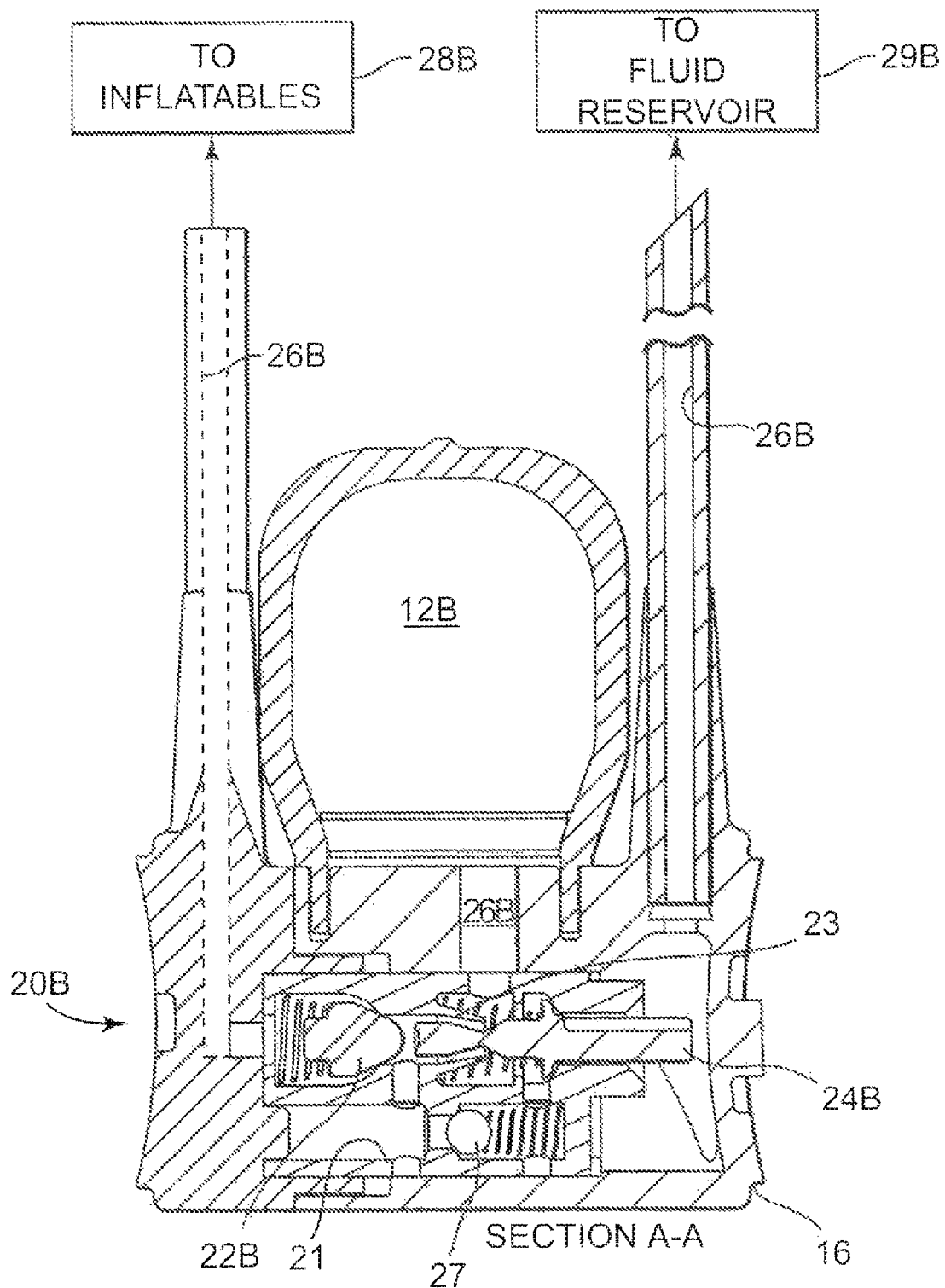
FIG. 8 is a sectional view of another embodiment of valve assembly for use with the present invention, which could also be taken approximately along lines A-A of FIG. 6

FIG. 8 shows another embodiment of valve assembly 20B suitable for use with the present invention. This example of valve assembly includes a spring biased poppet or ball valve 22B, a fluid bypass chamber 21, lip seal 23, ball valve 27, a spring biased suction poppet 24B and fluid passageways 26B for communicating with pump bulb 12B, inflatables 28B (e.g. penile prosthesis cylinders) and a fluid reservoir 29B.

The housing 16 also includes protrusions 18. The protrusions 18 should afford stabilization of the implant within tissue (e.g. the scrotum), afford tactile feedback to the patient and assist the patient in actuating the valve assembly.

The housing 16 is preferably bar shaped as shown in FIGS. 1-6, with end portions and side portions. Preferably, the end portions have at least three protrusions 18 total, preferably more. FIG. 4A is an engineering drawing of a preferred embodiment showing preferred dimensions for protrusions according to one embodiment of the present invention. The protrusions 18 have a preferred height of about 0.040 inches.

The housing 16 preferably includes two elongate sidebars or stabilizing fins 19 on the side portions. The fins 19 are sized, shaped and positioned to assist the patient in accessing and/or holding onto the pump. In some instances, the pump may tend to elevate relative to the patient's scrotum. In such cases, a patient may reach up to grab the pump and pull it down to access either the inflation or deflation area. Some patients lack manual dexterity. Such patients use two hands to inflate and/or deflate—one hand to hold the pump in place and one hand to either inflate or deflate. If the pump is constructed of a silicone elastomer (or other similar materials) and bathed in body fluids, the pump can be very slippery and hard to grasp. The fins 19 enhance the patient's grip on the side of the pump to pull it down and/or to hold onto the pump. The fins 19 operate in a manner similar to the way the protrusions on the bulb and deflation area operate to enhance the patient's grip for inflation and deflation. In a preferred embodiment, the fins 19 have a width of about 0.07 inches, a height of about 0.08 inches and a length of about 0.55 inches.

Figure 4:
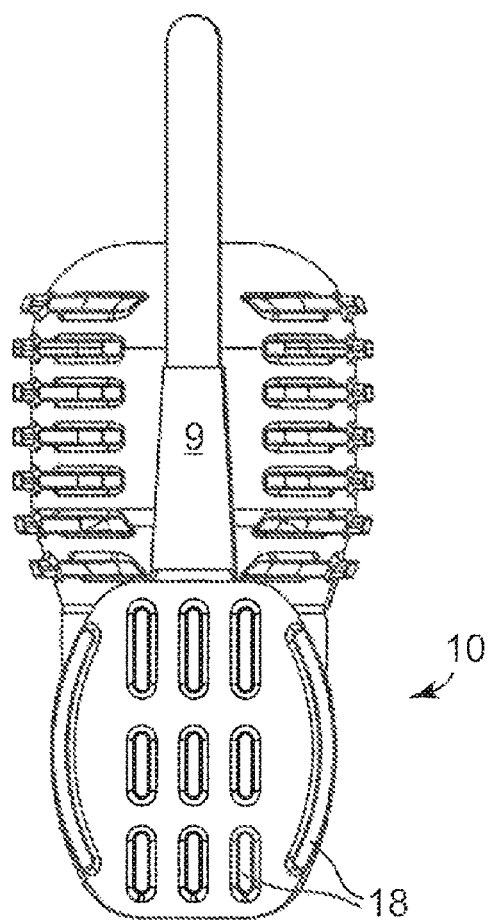
FIG. 4 is a right side view of the pump assembly of FIG. 1.
Figure 4A:
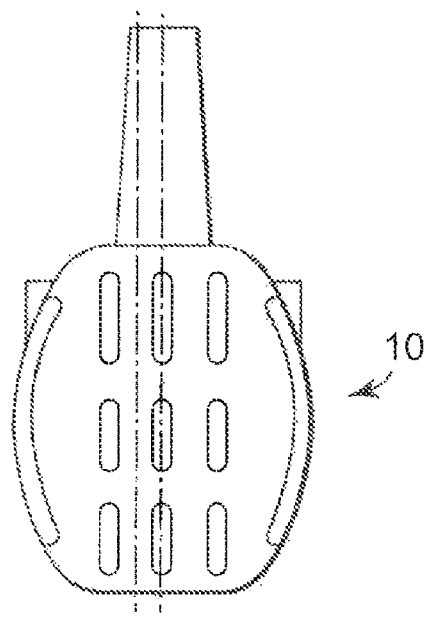
FIG. 4A is an end view of a component according to a preferred embodiment of the present invention.
Figure 5:
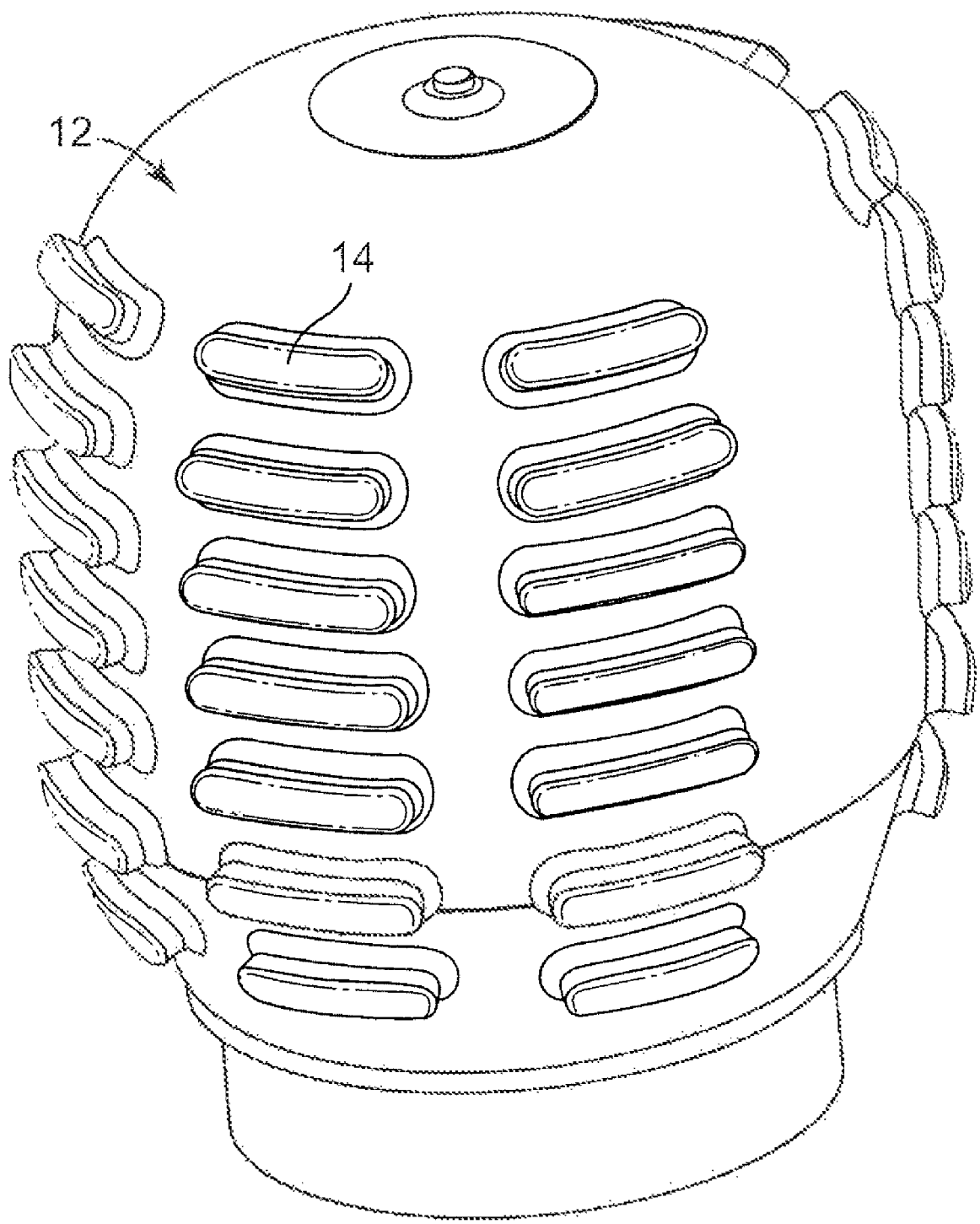
FIG. 5 is a perspective view of a pump bulb component of the pump assembly of FIG. 1.
Figure 6:
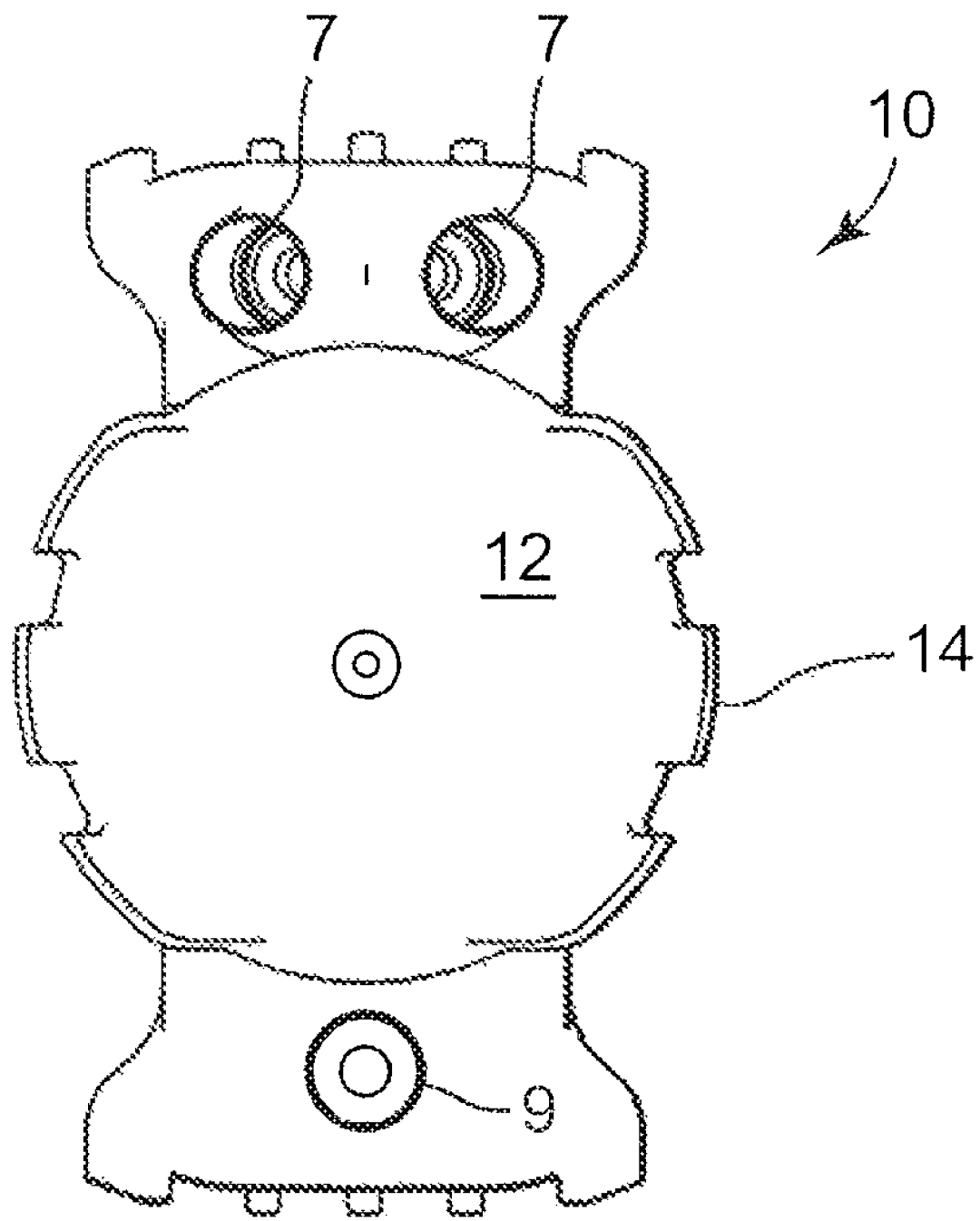
FIG. 6 is a top view of the pump assembly of FIG. 1.
Figure 9:
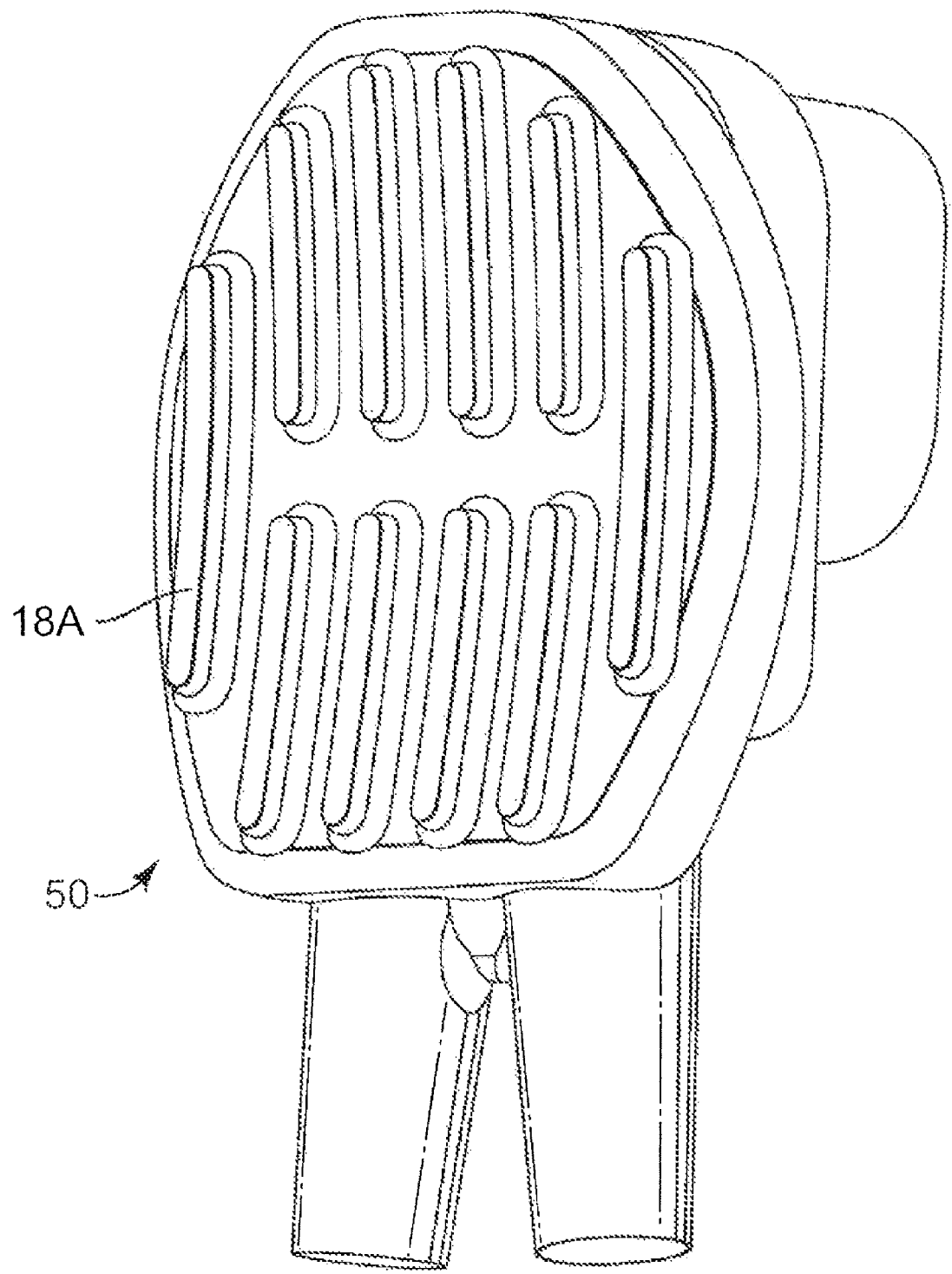
FIG. 9 is a perspective view of another component of a pump assembly according to another aspect of the present invention.
Figure 10:
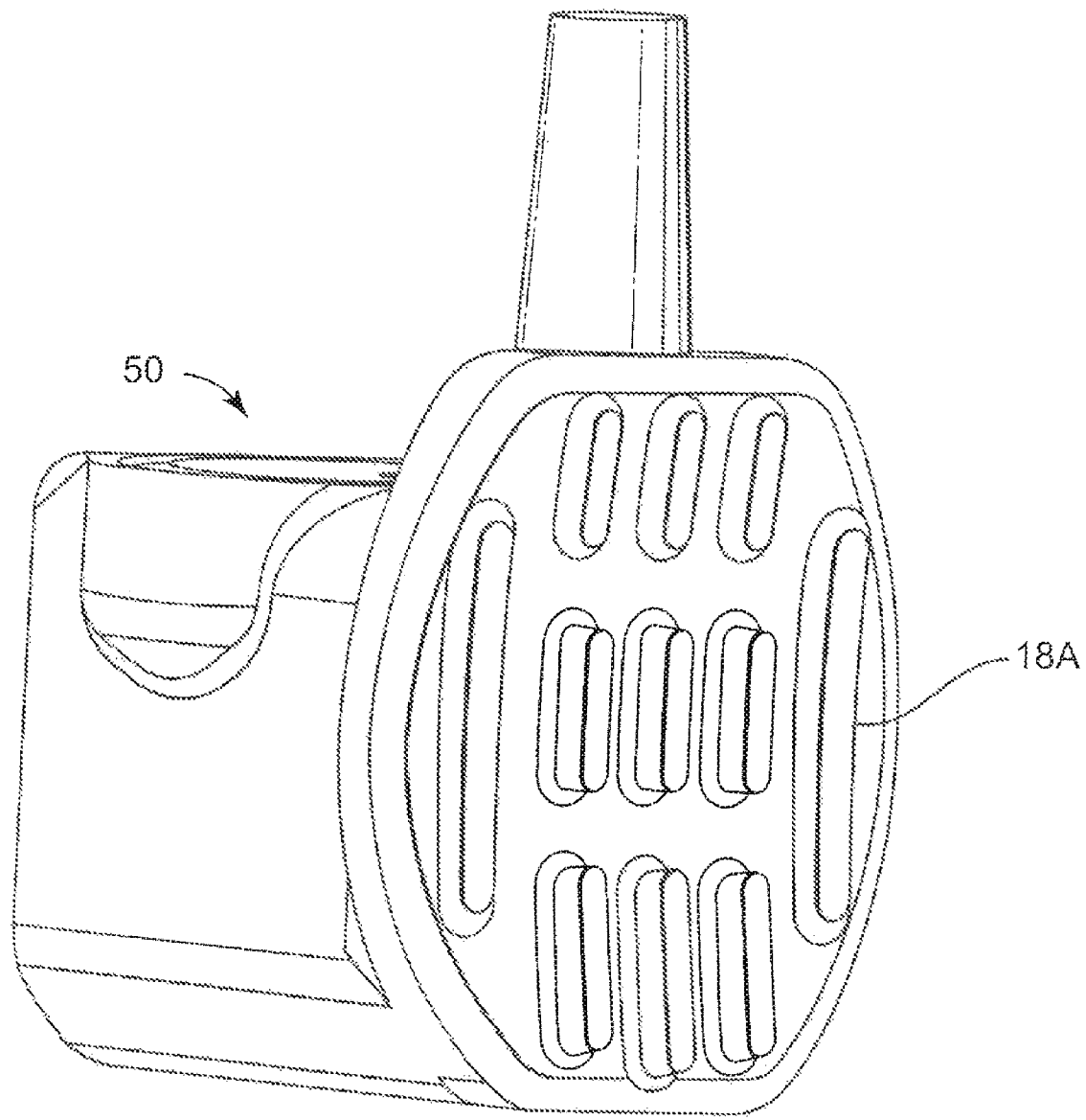
FIG. 10 is a perspective view of another component of a pump assembly according to another aspect of the present invention.

FIGS. 9 and 10 show another embodiment of portions of a pump assembly housing 50 that is similar to the housing 16 in FIG. 4, except that protrusions 18A are straight instead of arcuate shaped.

Figure 12:
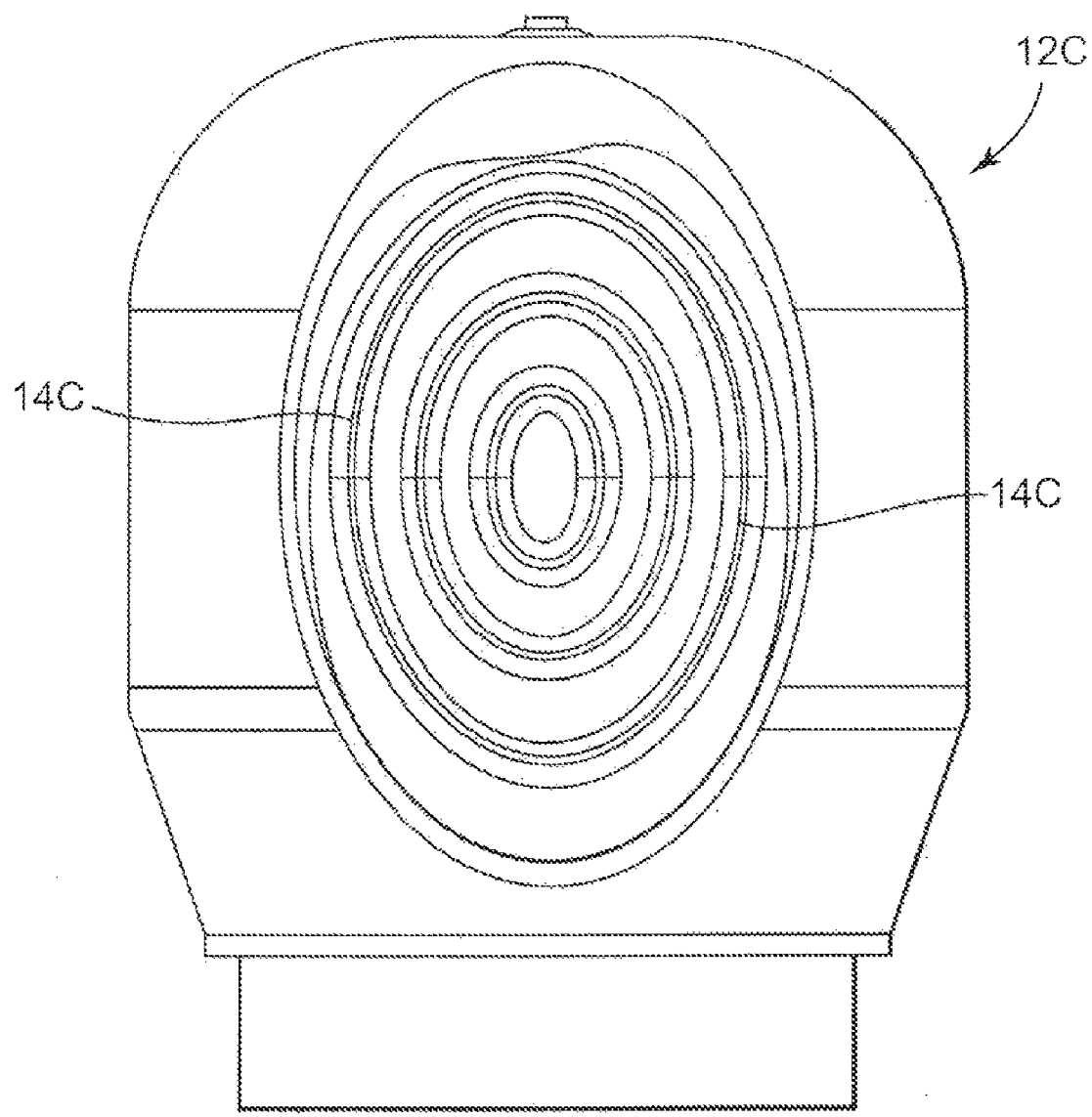
FIG. 12 is a front view of a pump bulb component according to another aspect of the present invention.
Figure 13:
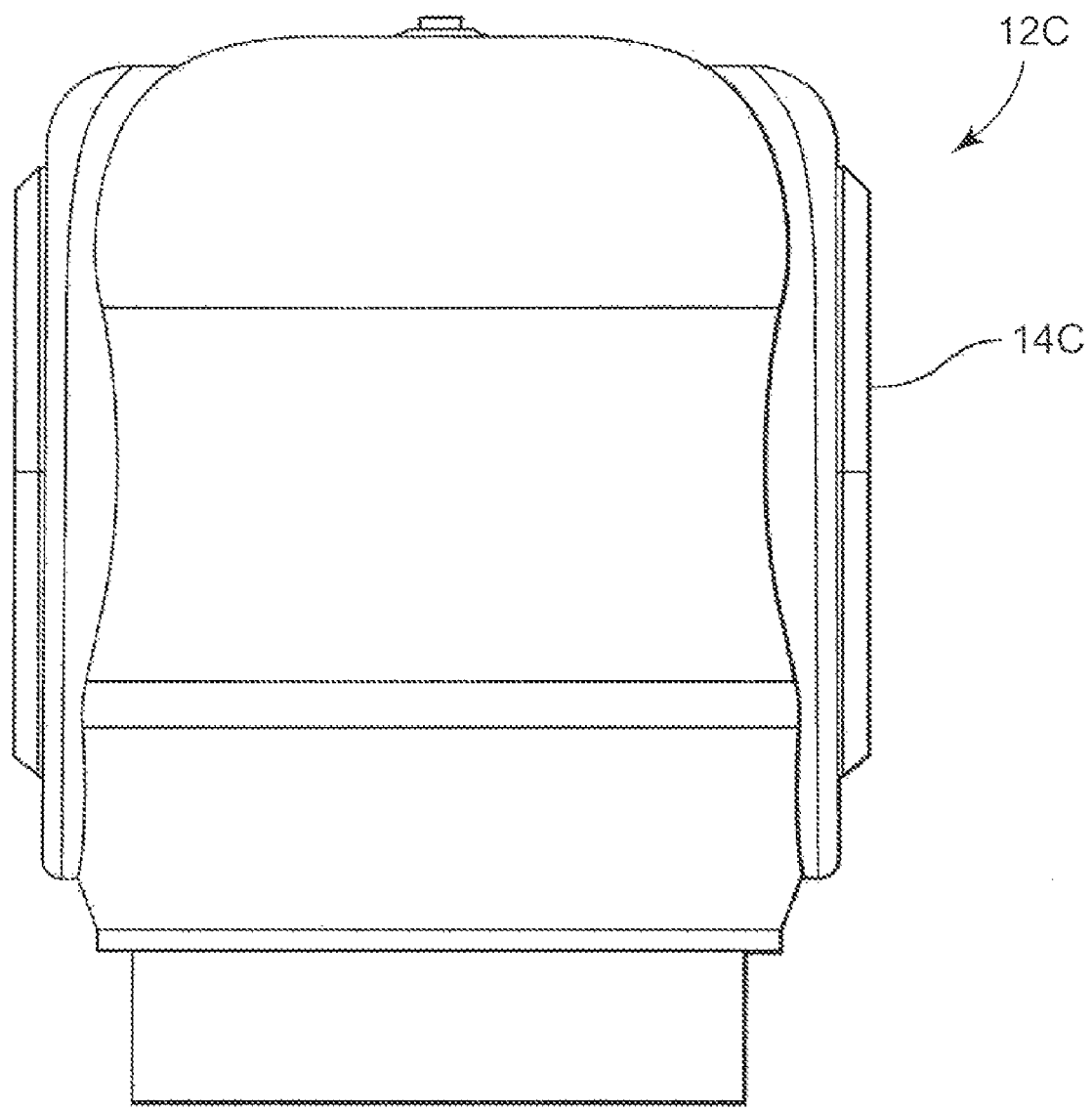
FIG. 13 is a side view of the component of FIG. 12.

FIGS. 12 and 13 show another embodiment of component or portion of pump bulb 12C according to the present invention. In this embodiment, the protrusions 14C are oval shaped rather than linear. The protrusions 14C and intervening grooves/valleys are believed to resist slippage in three mutually perpendicular directions.

Figure 14:
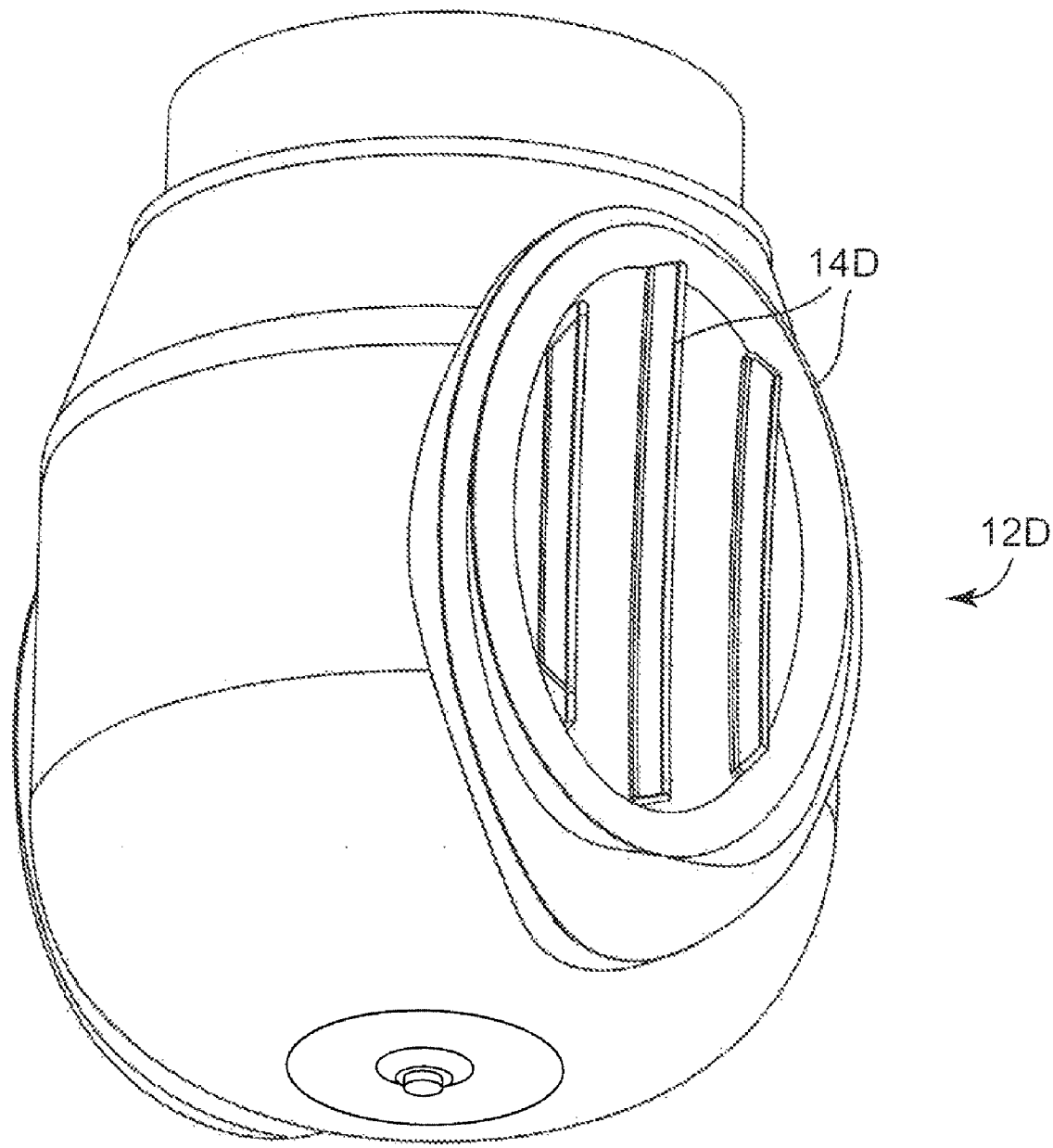
FIG. 14 is a perspective view of a pump bulb component according to another aspect of the present invention.
Figure 15:
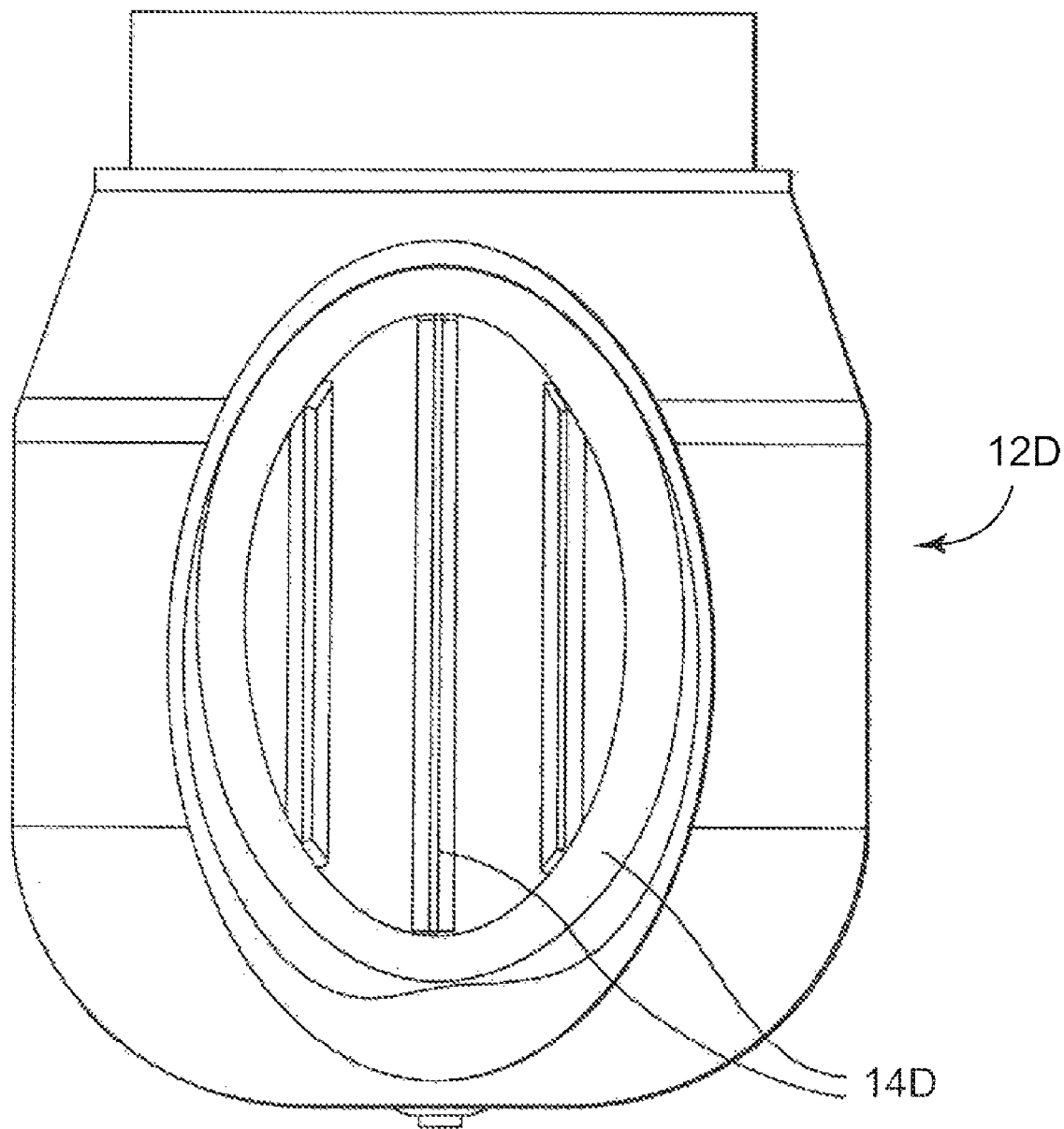
FIG. 15 is a front view of the component of FIG. 14.
Figure 16:
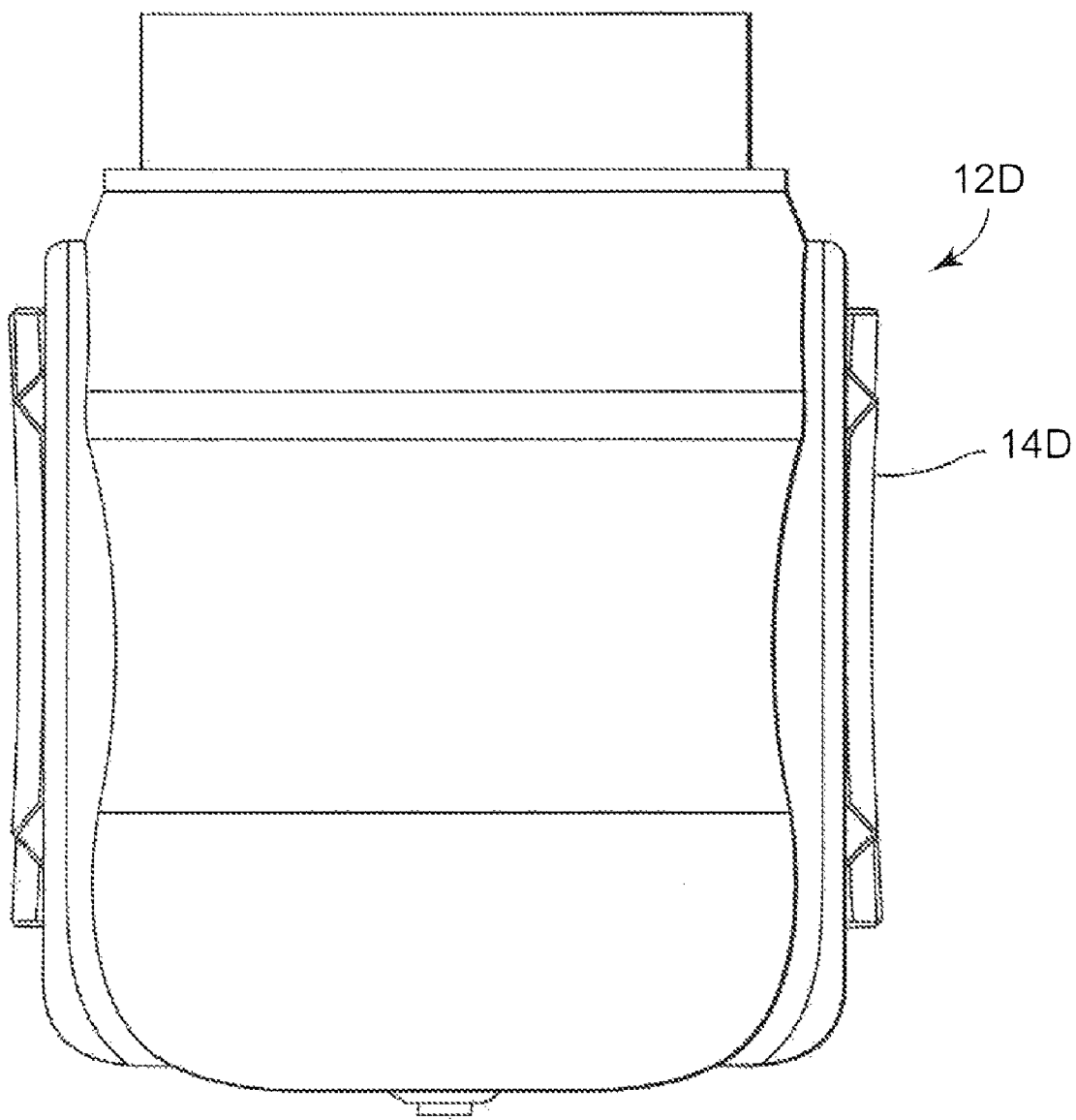
FIG. 16 is a side view of the component of FIG. 14.

FIGS. 14 through 16 show another embodiment of component or portion of pump bulb 12D according to the present invention. In this embodiment, the protrusions 14D are a combination of straight and arcuate shaped structures. The straight protrusions afford a relative sharp configuration at its top.

Figure 17:
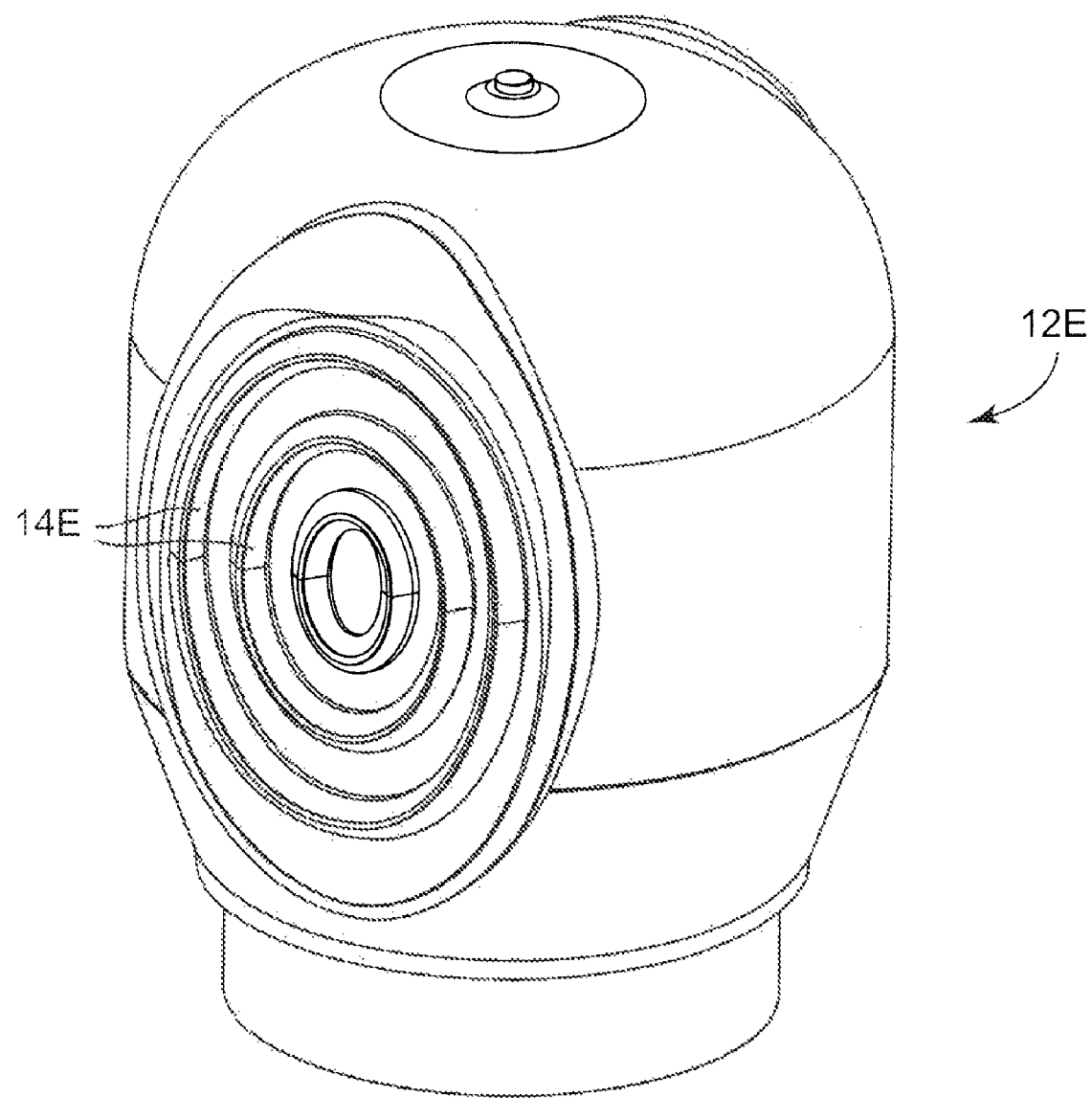
FIG. 17 is a perspective view of a pump bulb component according to another aspect of the present invention.

FIG. 17 shows a pump bulb 12E with circular protrusions 14E. The protrusions and intervening grooves/valleys are believed to resist slippage in three mutually perpendicular directions.

Figure 18:
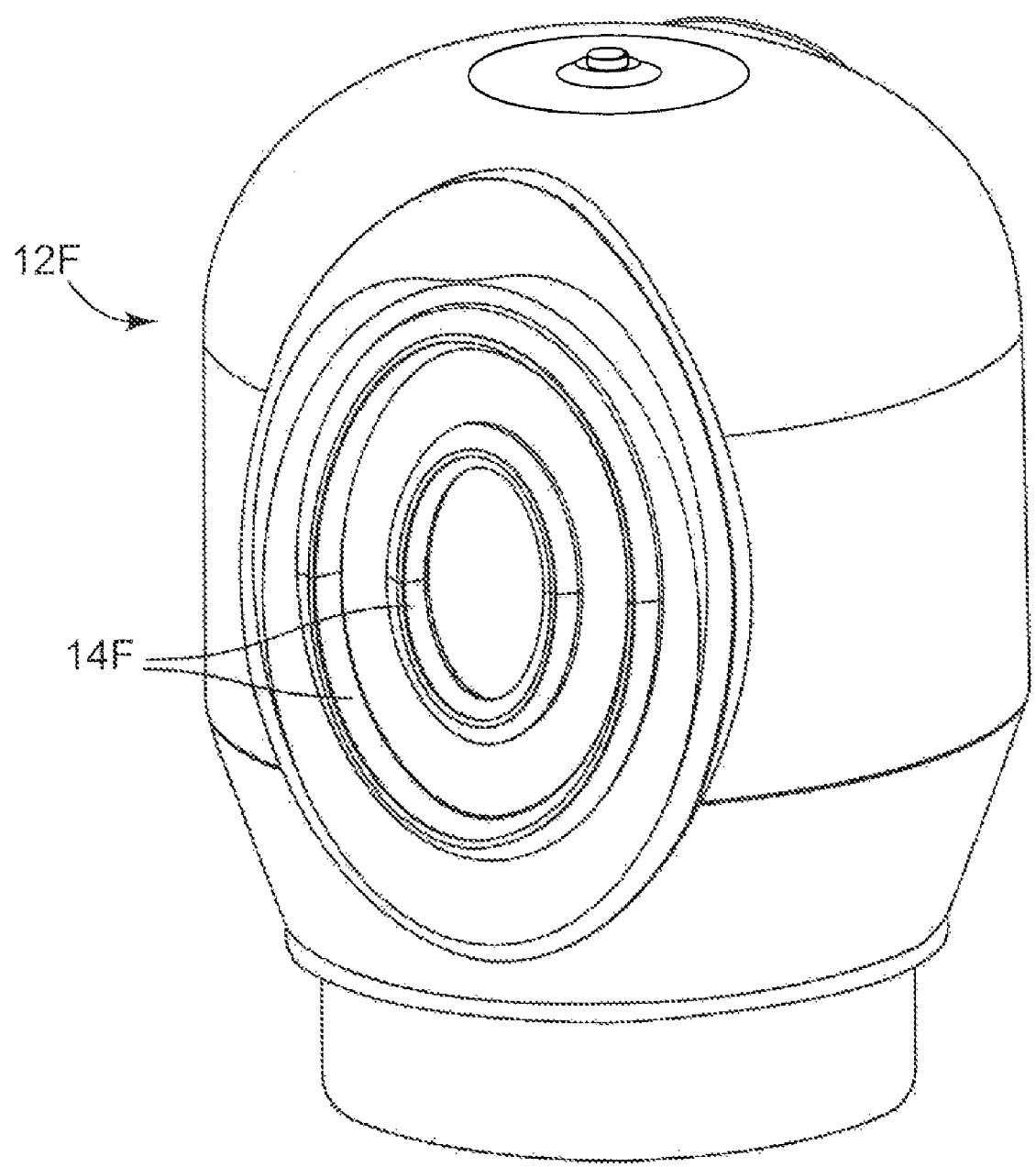
FIG. 18 is a perspective view of a pump bulb component according to another aspect of the present invention.
Figure 19:
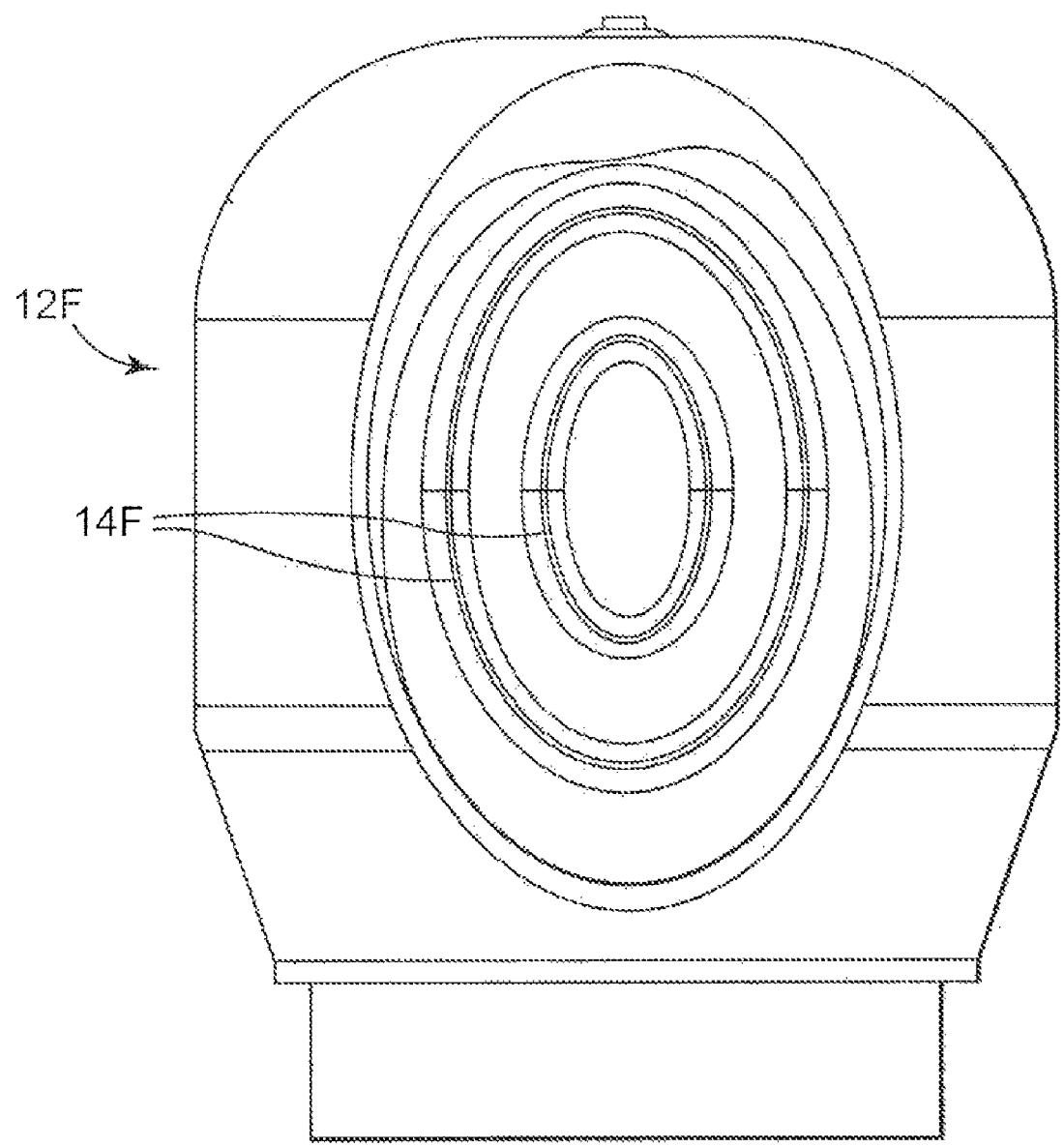
FIG. 19 is a front view of the component of FIG. 18.
Figure 20:
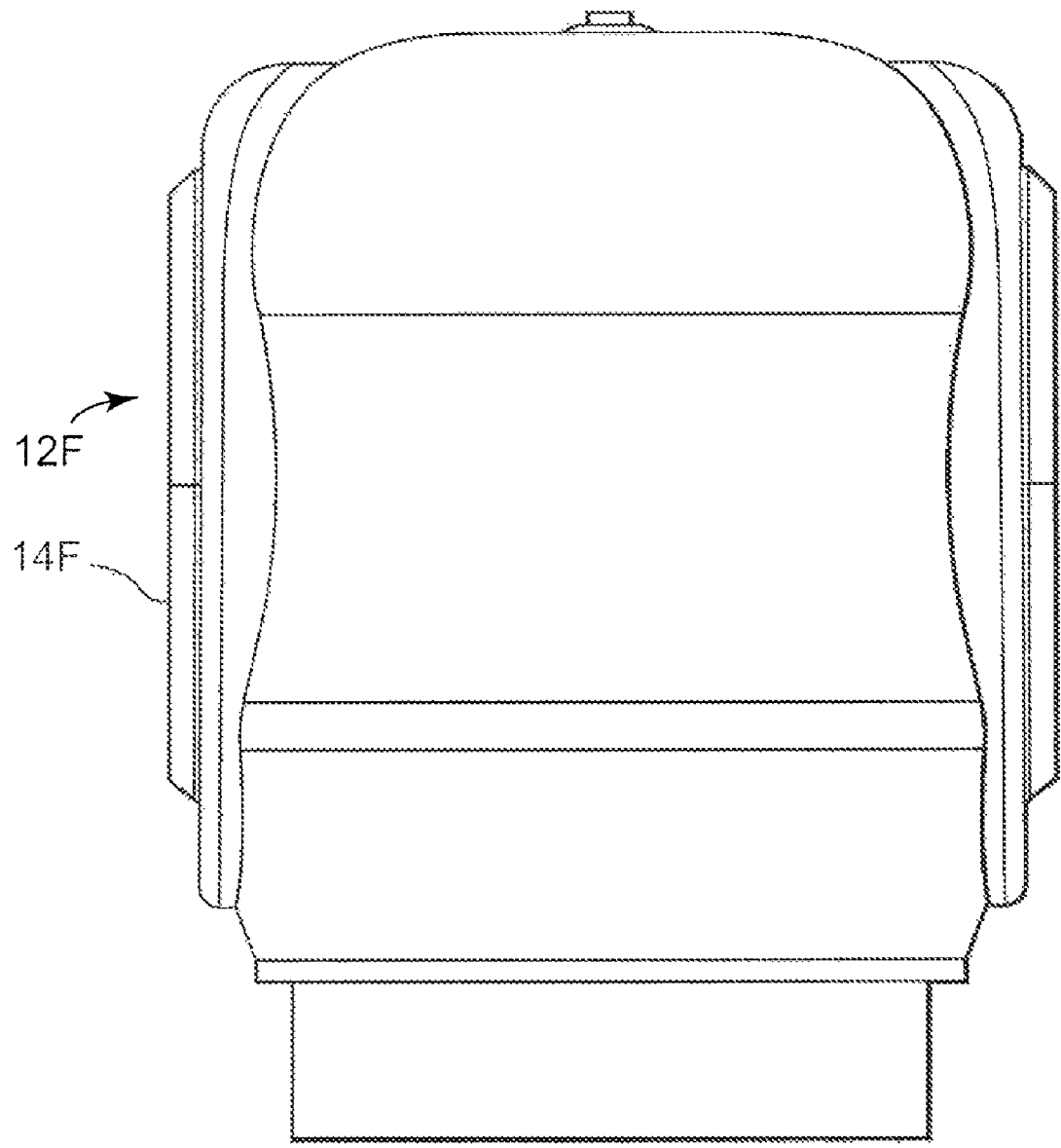
FIG. 20 is a side view of the component of FIG. 18.

FIGS. 18 through 20 show a pump bulb 12F with generally elliptically shaped protrusions 14F.

Figure 21:
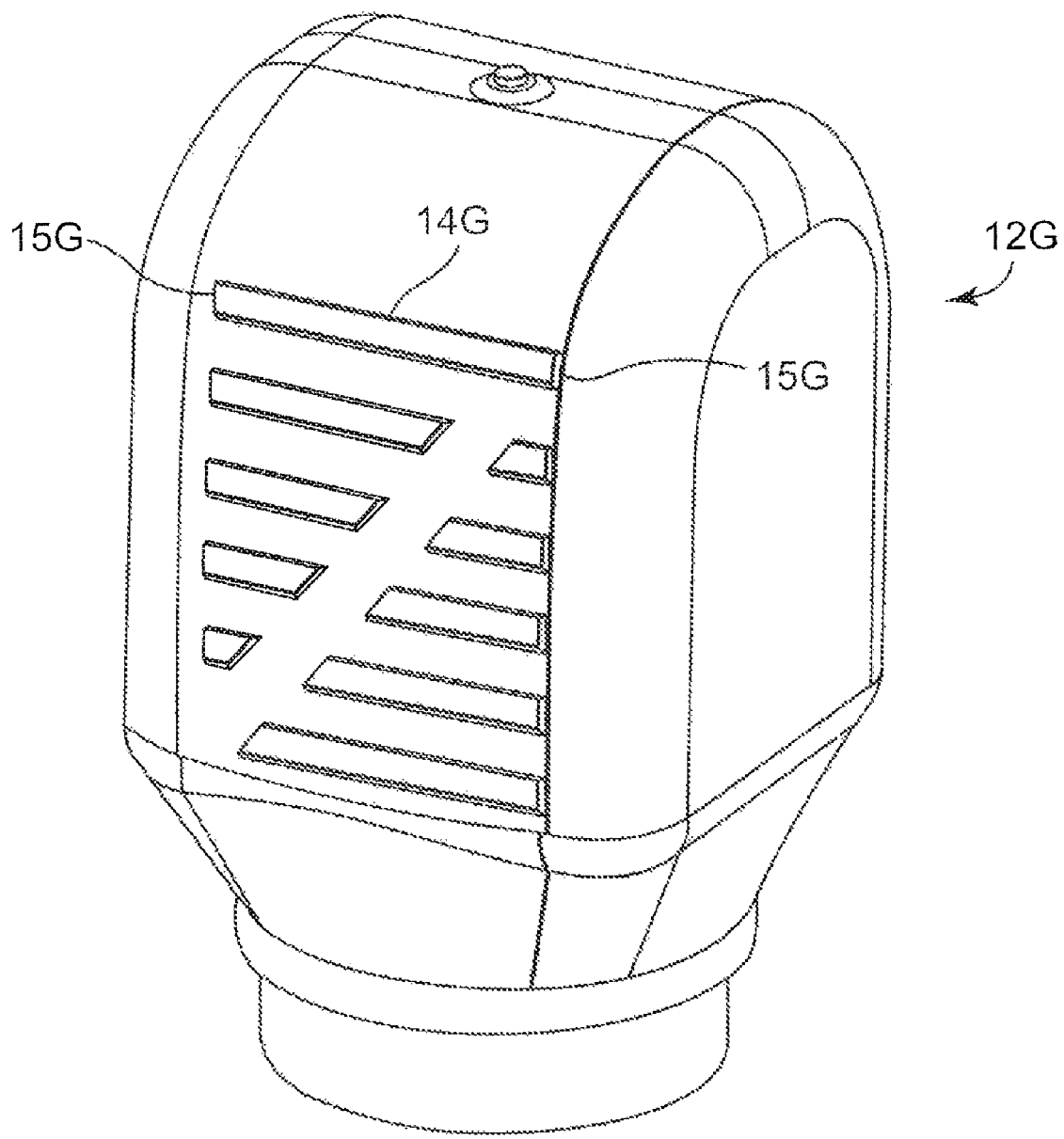
FIG. 21 is a perspective view of a pump bulb component according to another aspect of the present invention.

FIG. 21 shows a pump bulb 12G with substantially linearly extending protrusions 14G with ends 15G.

Figure 22:
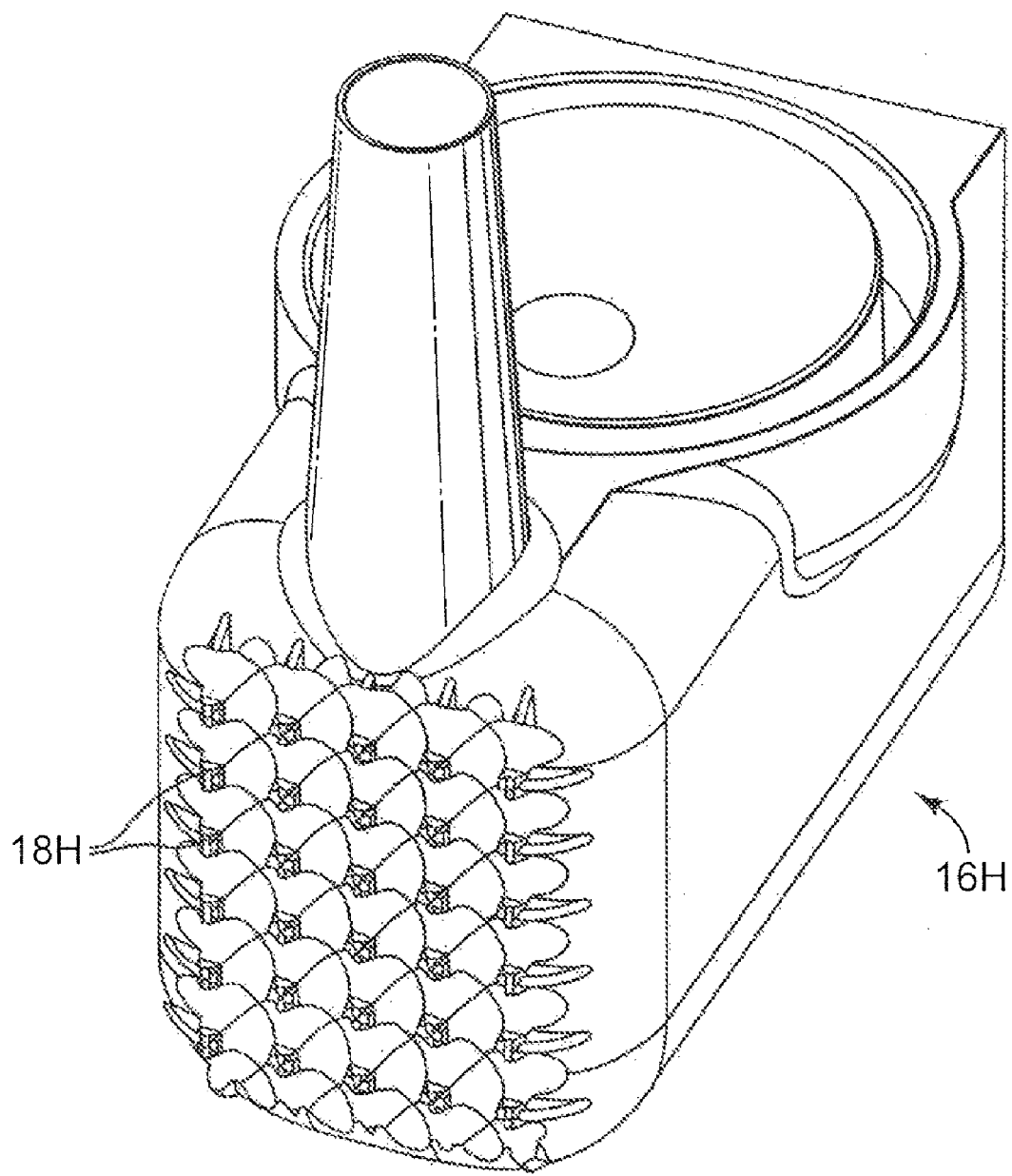
FIG. 22 is a perspective view of a pump housing component according to another aspect of the present invention.

FIG. 22 shows a portion of a pump housing 16H and a plurality of protrusions 18H. Preferably, the tips of the protrusions 18H are relatively sharp but so sharp that they unduly irritate or damage tissue.

Figure 23:
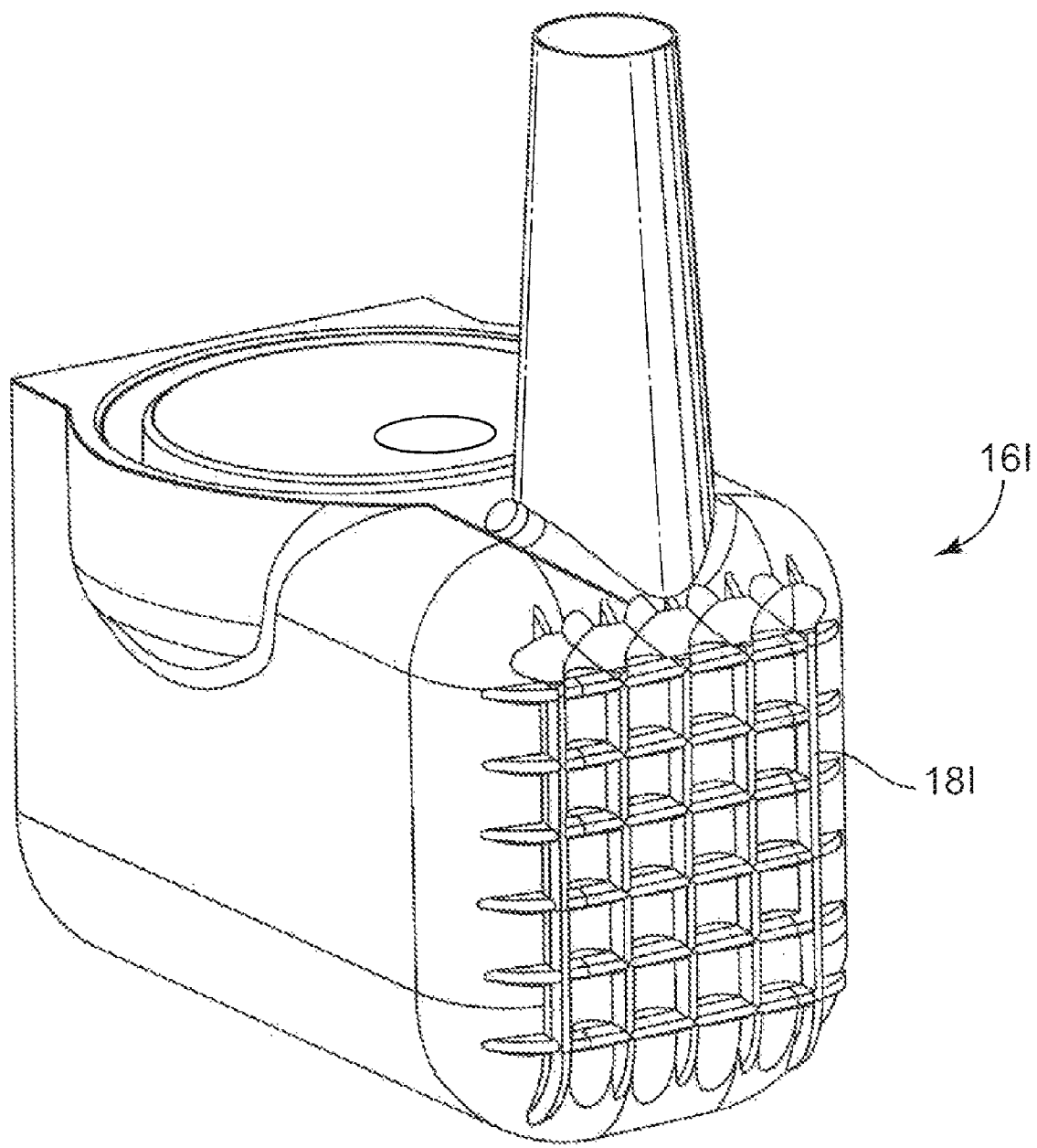
FIG. 23 is a perspective view of a pump housing component according to another aspect of the present invention.

FIG. 23 shows a portion of a pump housing 16I and a plurality of protrusions 18I.

Figure 24:
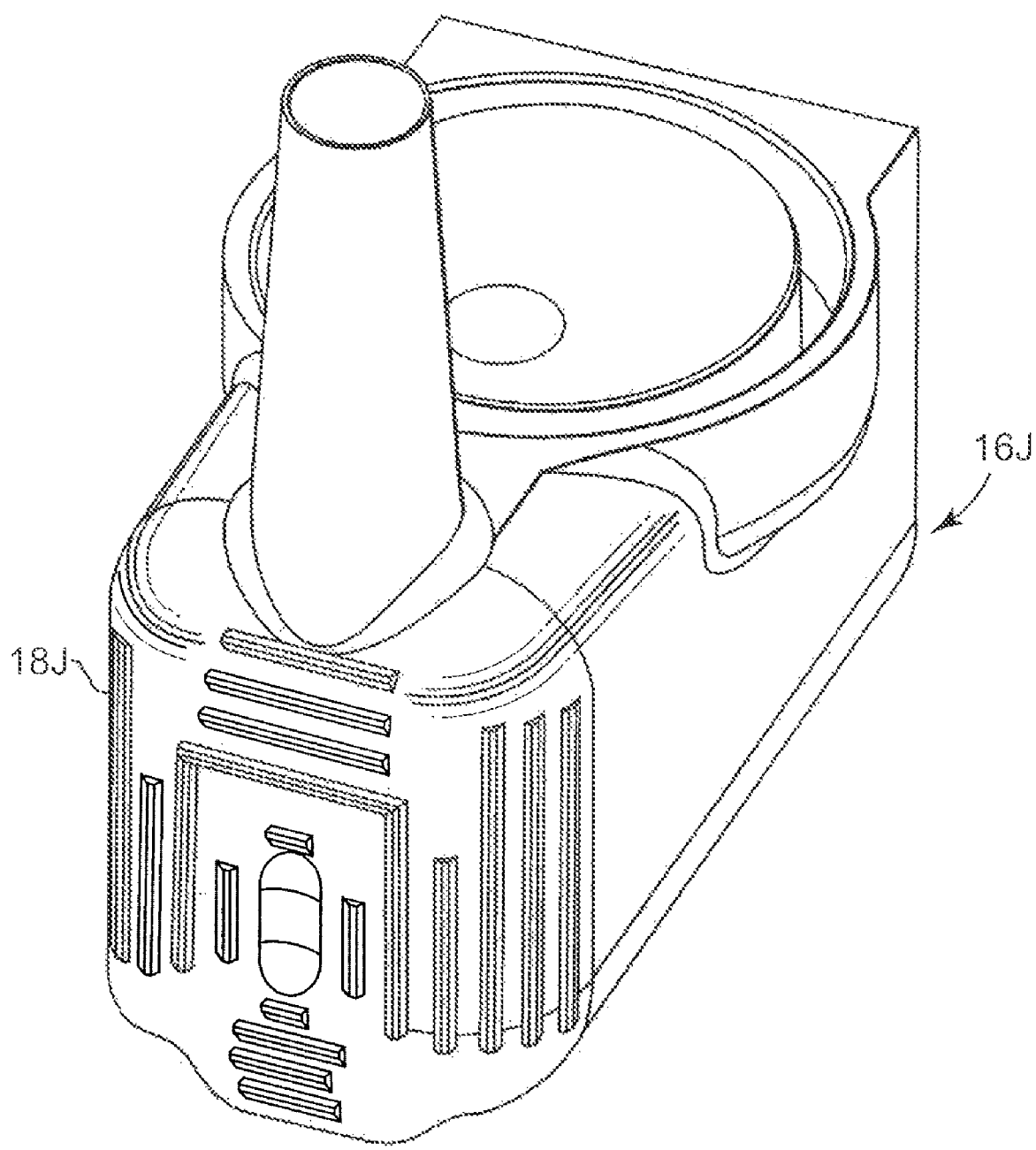
FIG. 24 is a perspective view of a pump housing component according to another aspect of the present invention.

FIG. 24 shows a portion of a pump housing 16J and a plurality of protrusions 18J.

Figure 26:
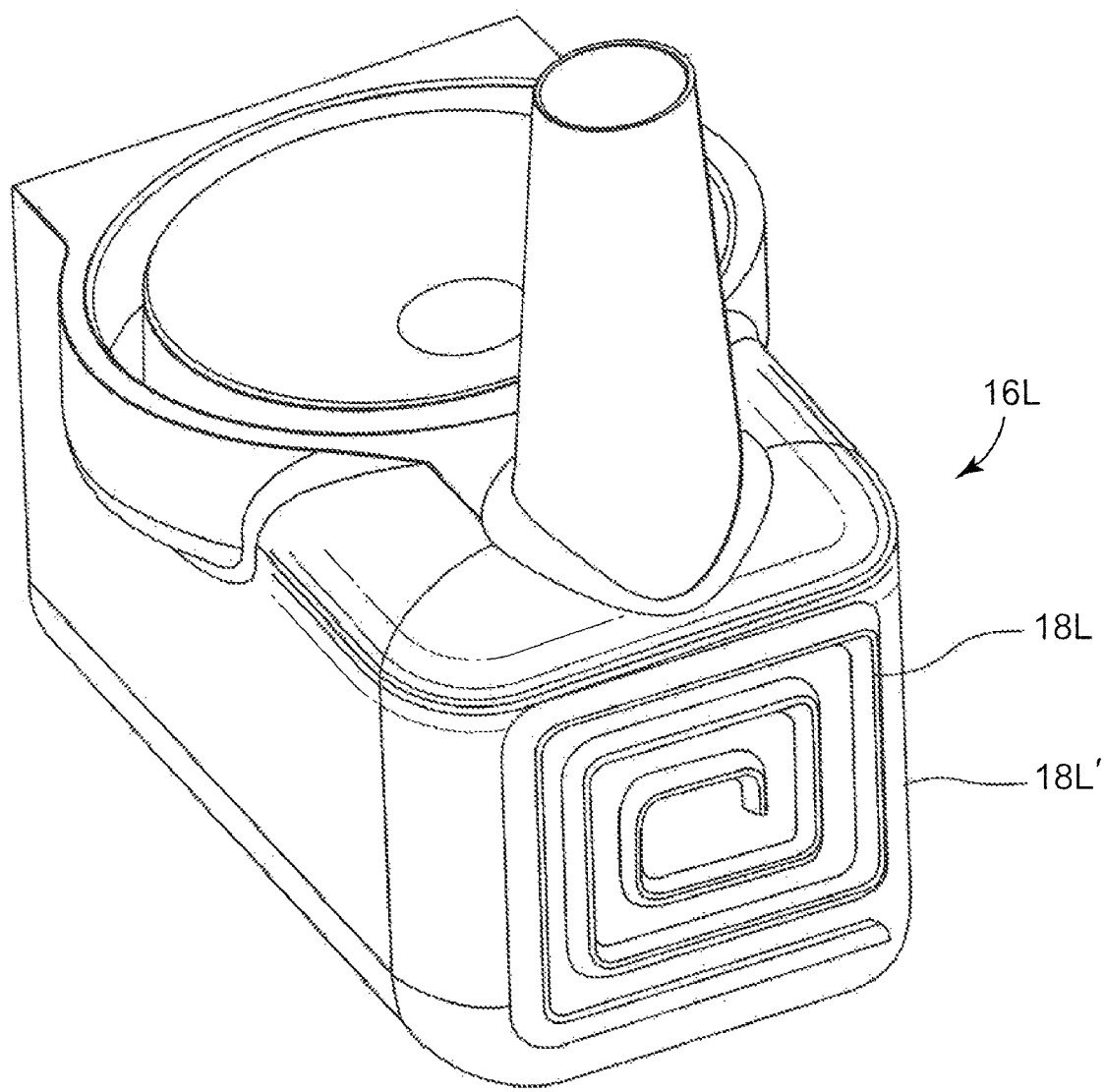
FIG. 26 is a perspective view of a pump housing component according to another aspect of the present invention.

FIG. 26 shows a portion of a pump housing 16L and a plurality of protrusions 18L. The protrusions comprise a maze shaped protrusion 18L and a plurality of partial sphere shaped protrusions 18L'.

Figure 28:
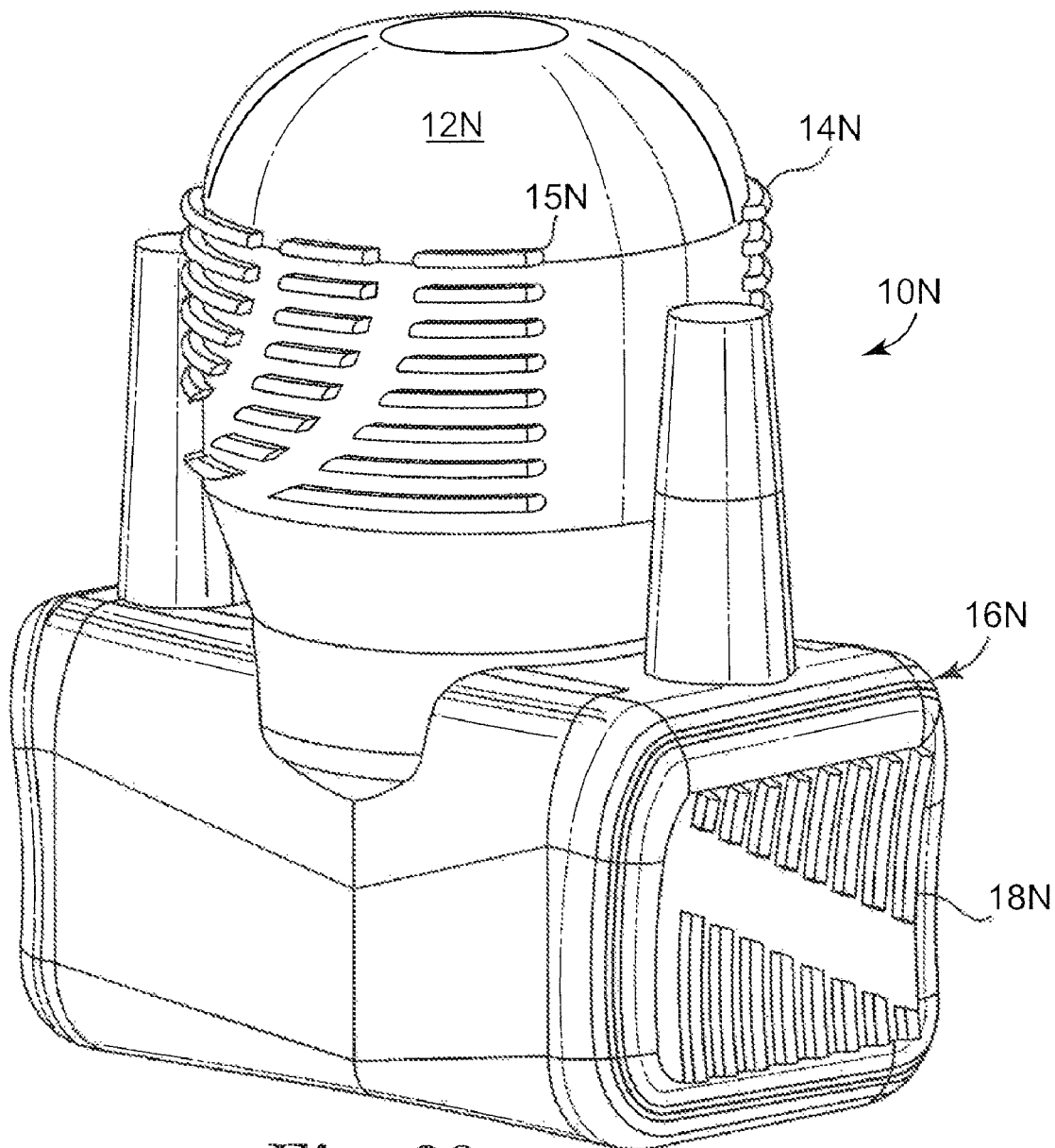
FIG. 28 is a perspective view of another aspect of pump assembly according to the present invention.

FIG. 28 shows another embodiment of pump assembly 10N according to the present invention. The pump assembly 10N includes a pump bulb 12N with protrusions 14N having ends 15N, pump housing 16N and protrusions 18N.

Figure 29:
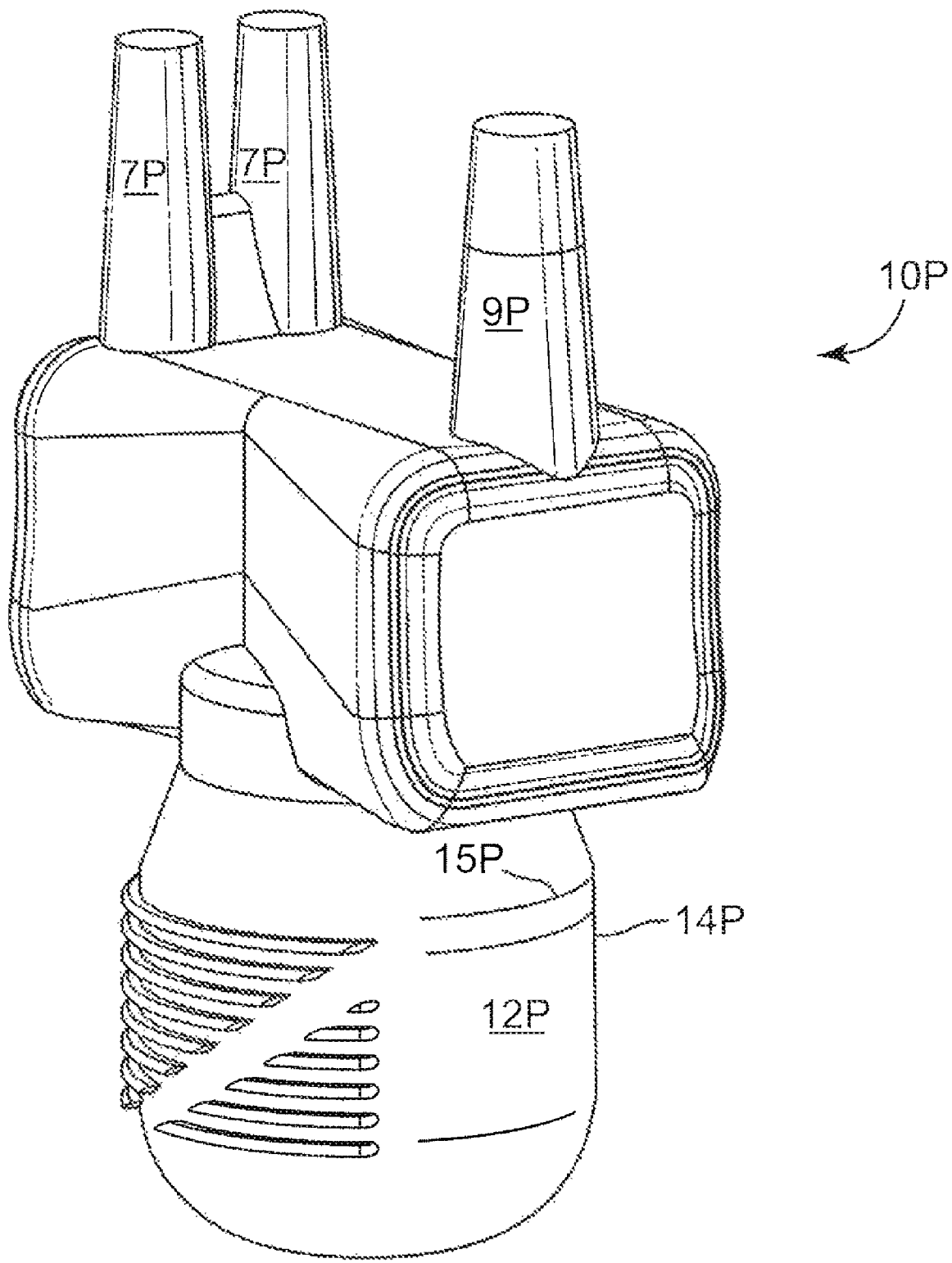
FIG. 29 is a perspective view of another aspect of pump assembly according to the present invention.

Notably, the pump bulb need not be on the same side of the pump housing as the connection to the inflatable members and reservoir. FIG. 29 shows a pump assembly 10P includes a pump bulb 12P with protrusions 14P having ends 15P, pump housing 16P and fluid connectors 7P and 9P.

Figure 30:
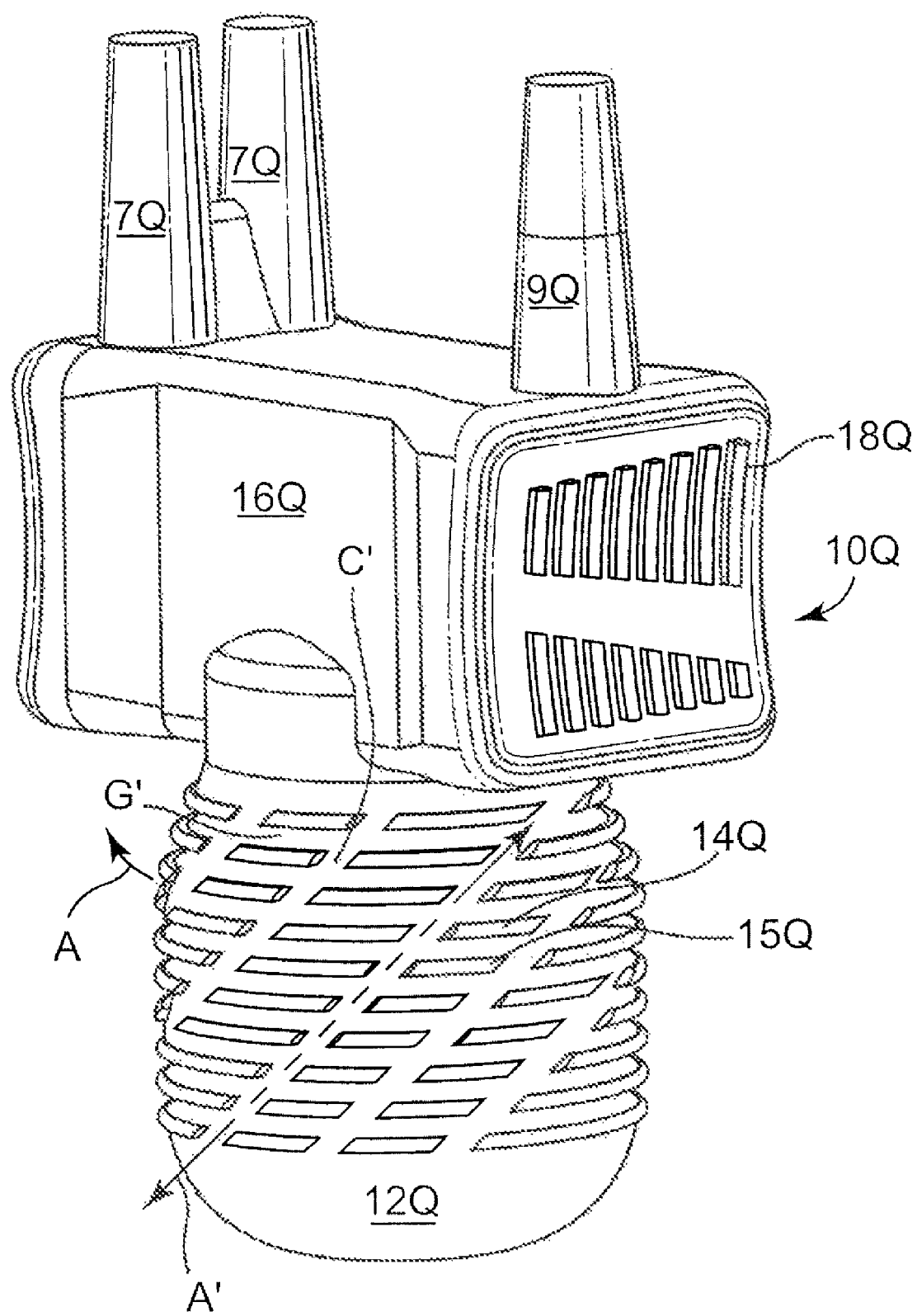
FIG. 30 is a perspective view of another aspect of pump assembly according to the present invention.
Figure 31:
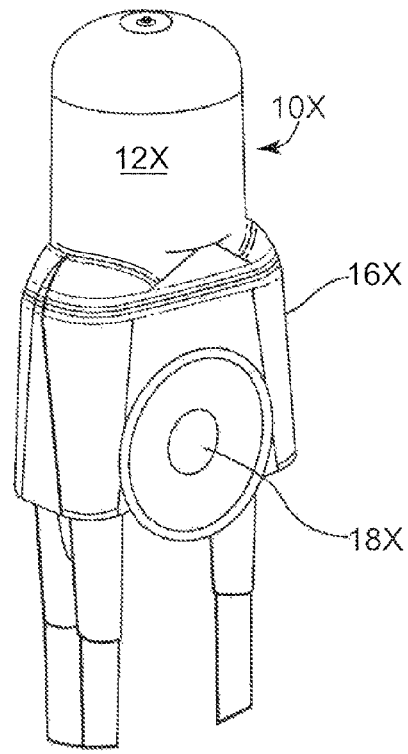
FIG. 31 is a perspective view of another aspect of pump assembly according to another aspect of the present invention.
Figure 32:
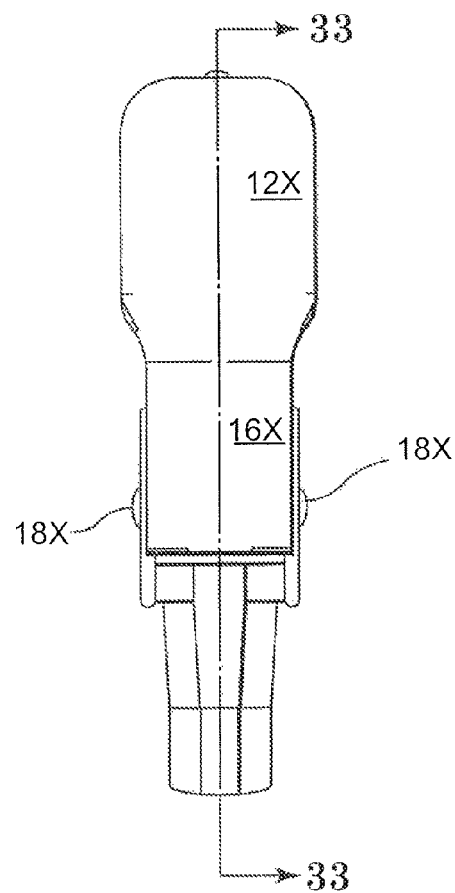
FIG. 32 is a side view of FIG. 31.

Also notably, the grooves and channels for the protrusions need not be at right angles or continuous. FIG. 30 shows a pump assembly 10Q that includes a pump bulb 12Q with protrusions 14Q having ends 15Q, pump housing 16Q and fluid connectors 7Q and 9Q. The axis A of grooves G' formed by the protrusions 14Q is at a non-normal angle relative to the axis A' of channels C'.

Figure 33:
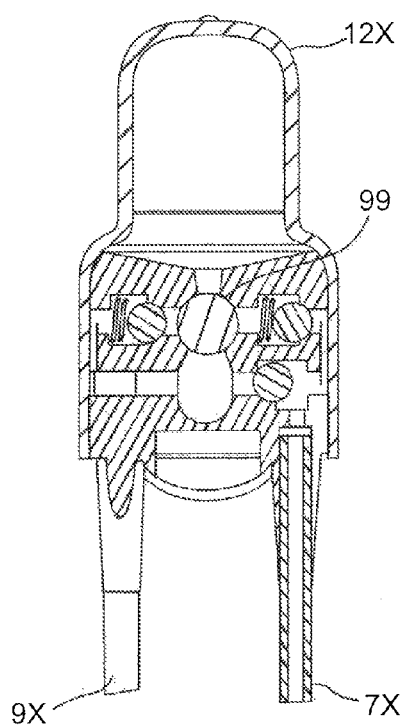
FIG. 33 is a sectional view taken approximately along lines 33-33 of FIG. 32, which sectional view shows the pump assembly in an auto deflate/lock-out position.
Figure 34:
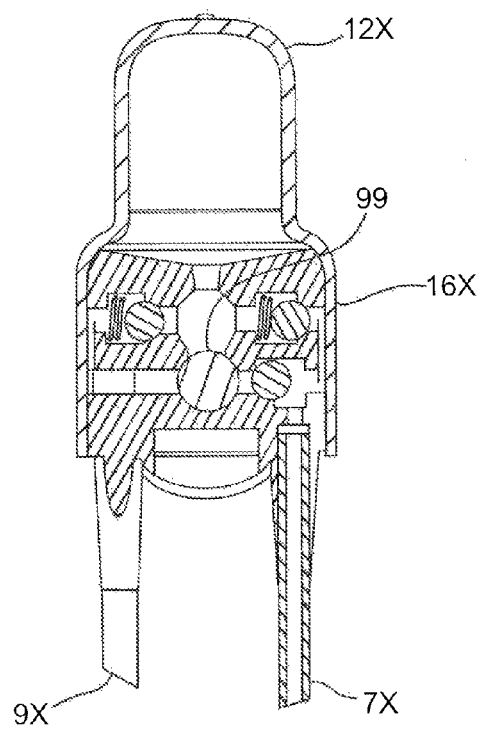
FIG. 34 is a sectional view taken approximately along lines 33-33 of FIG. 32, which sectional view shows the pump assembly in an active suction/pumping position.

Referring now to FIGS. 31 through 34, there is shown another embodiment of pump assembly 10X according to the present invention. The pump assembly includes fluid communication members 7X and 9X, pump bulb 12X, housing 16X, protrusions 18X and internal valve sphere 99. FIG. 34 is a cross section view of the pump assembly in the active suction/pumping position. FIG. 33 is a cross sectional view of the pump assembly in the auto deflate/lock-out position.

A well defined concave protrusion 18X is shown comprising a raised palpable button for locating the auto deflate area. In the active position, the sphere 99 blocks the deflate fluid channel and prevents pressurized fluid in the cylinders (see line 9X) returning to the reservoir (see line 7X). In the auto-deflate position, pressurized fluid in the cylinders is allowed to return to the reservoir unassisted by the patient holding the pump to obtain maximum flaccidity, the patient need only bend or squeeze the cylinders without manipulating the pump. Alternatively, a square deflation feature may be utilized.

Figure 35:
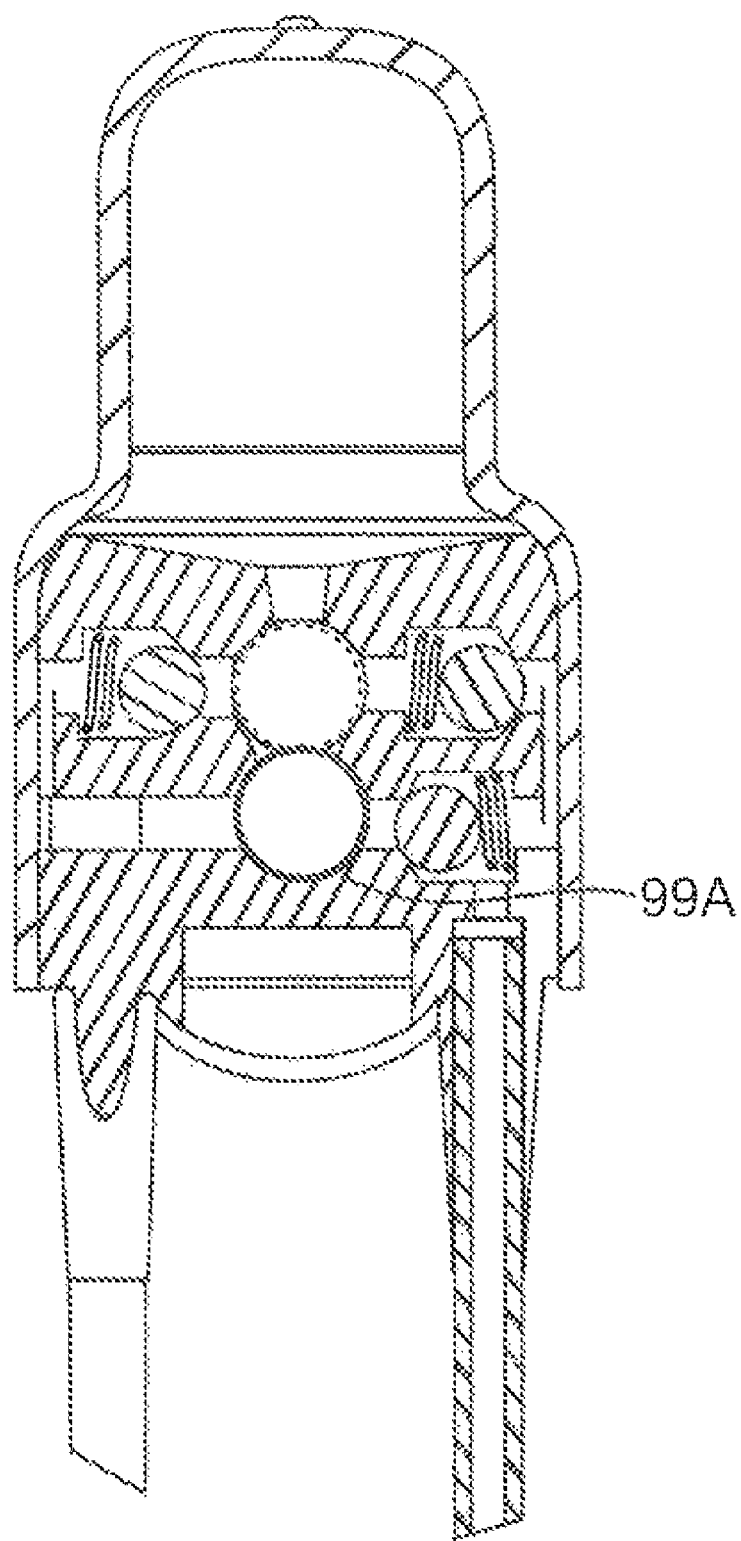
FIG. 35 is a sectional view of another embodiment of pump assembly according to the present invention, which view shows a sphere in a deflate/lockout position with dashed lines and in an active (pumping) position in solid lines.
Figure 36:
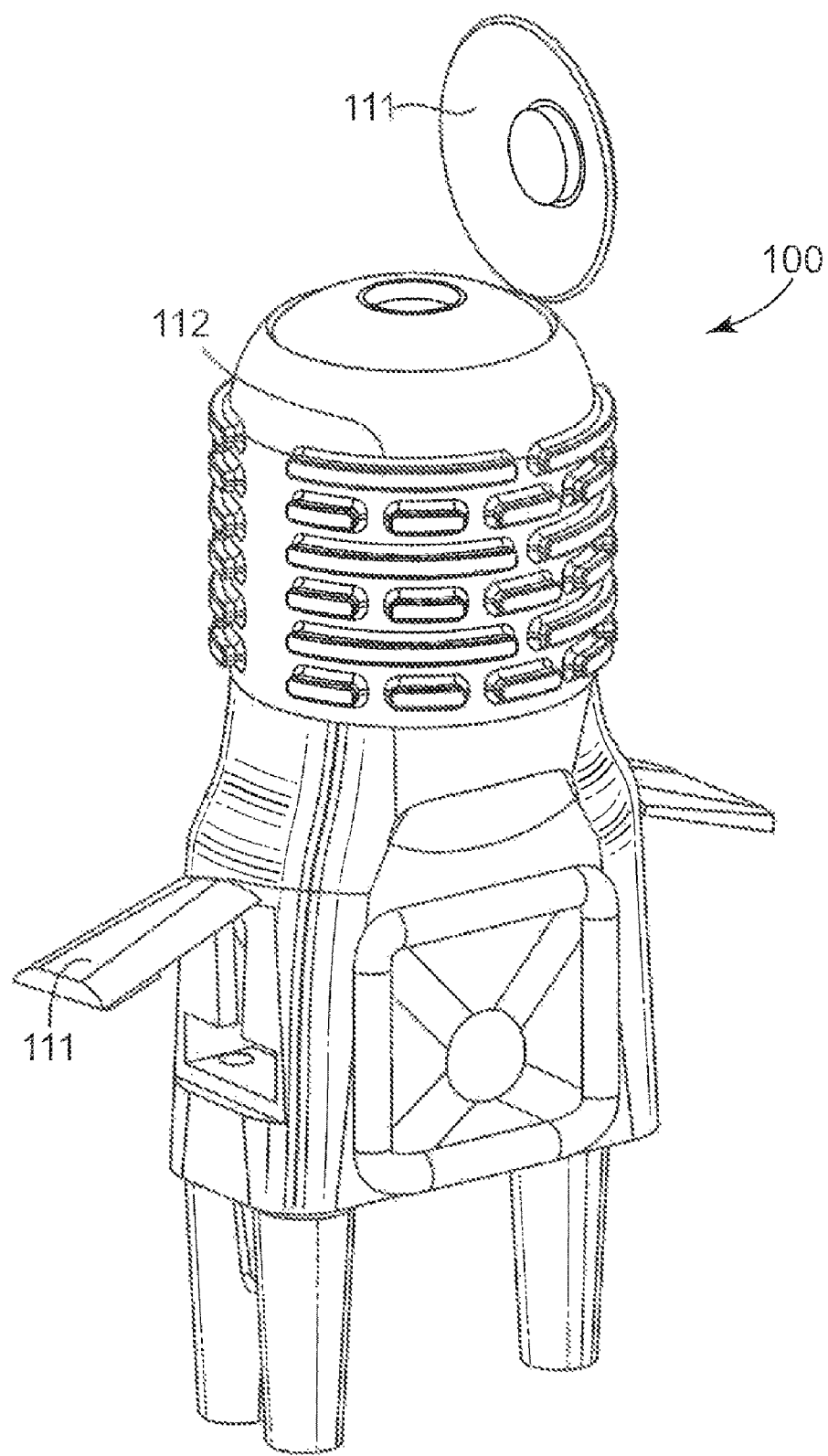
FIG. 36 is a perspective view of an alternative embodiment of housing with protrusions according to the present invention.
Figure 37:
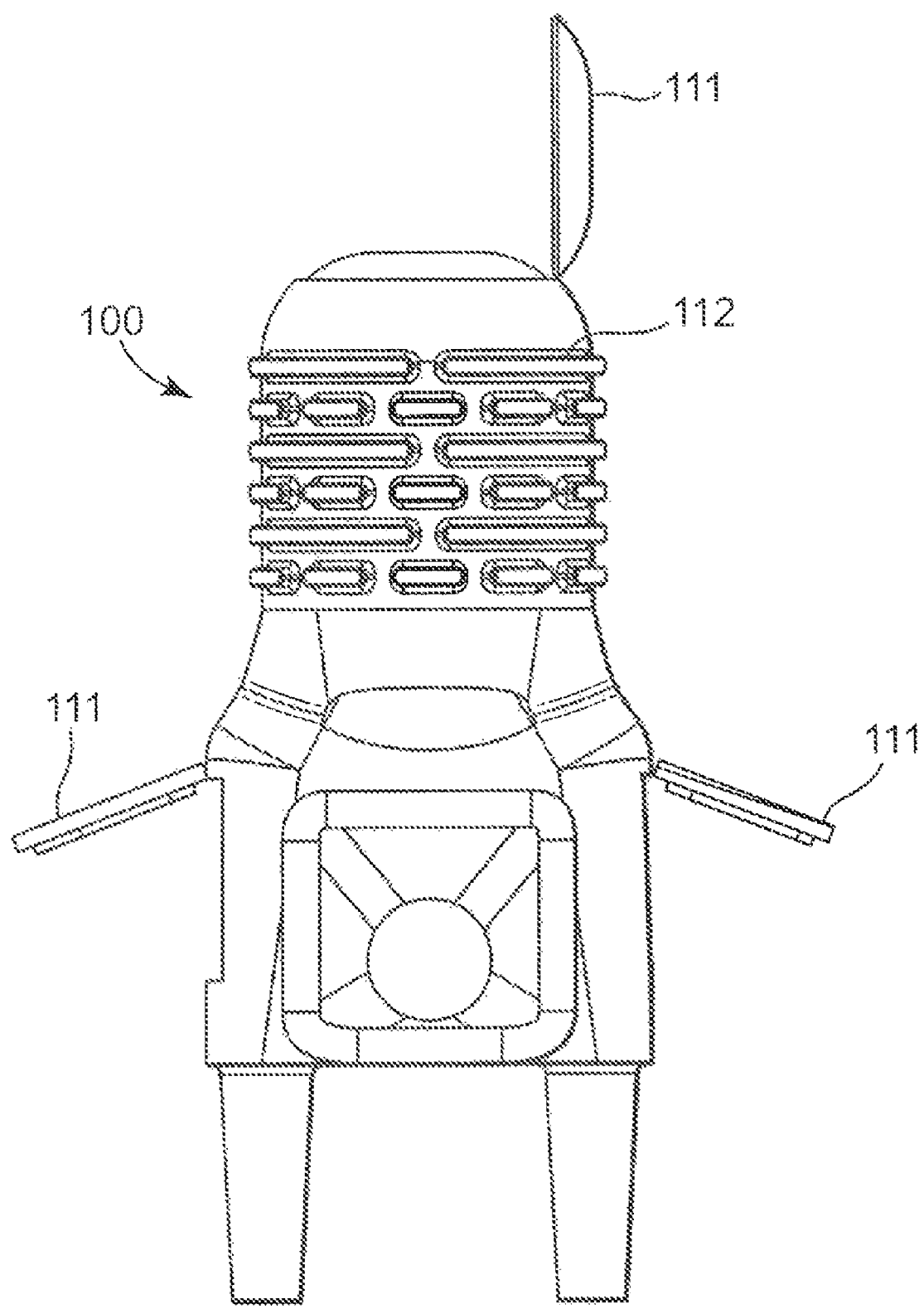
FIG. 37 is a side view of the housing of FIG. 36.
Figure 38:
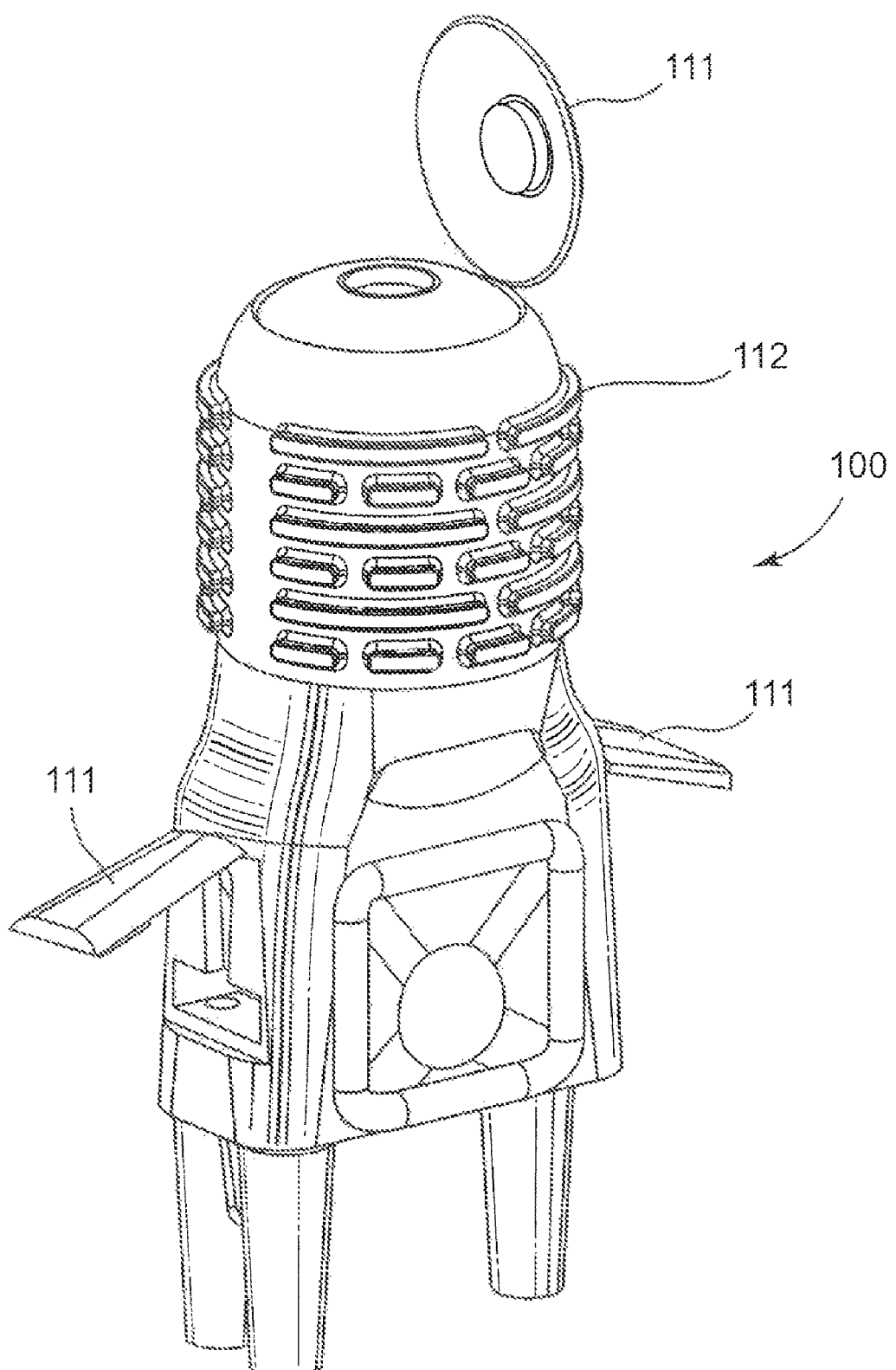
FIG. 38 is a perspective view of the housing of FIG. 36.
Figure 39:
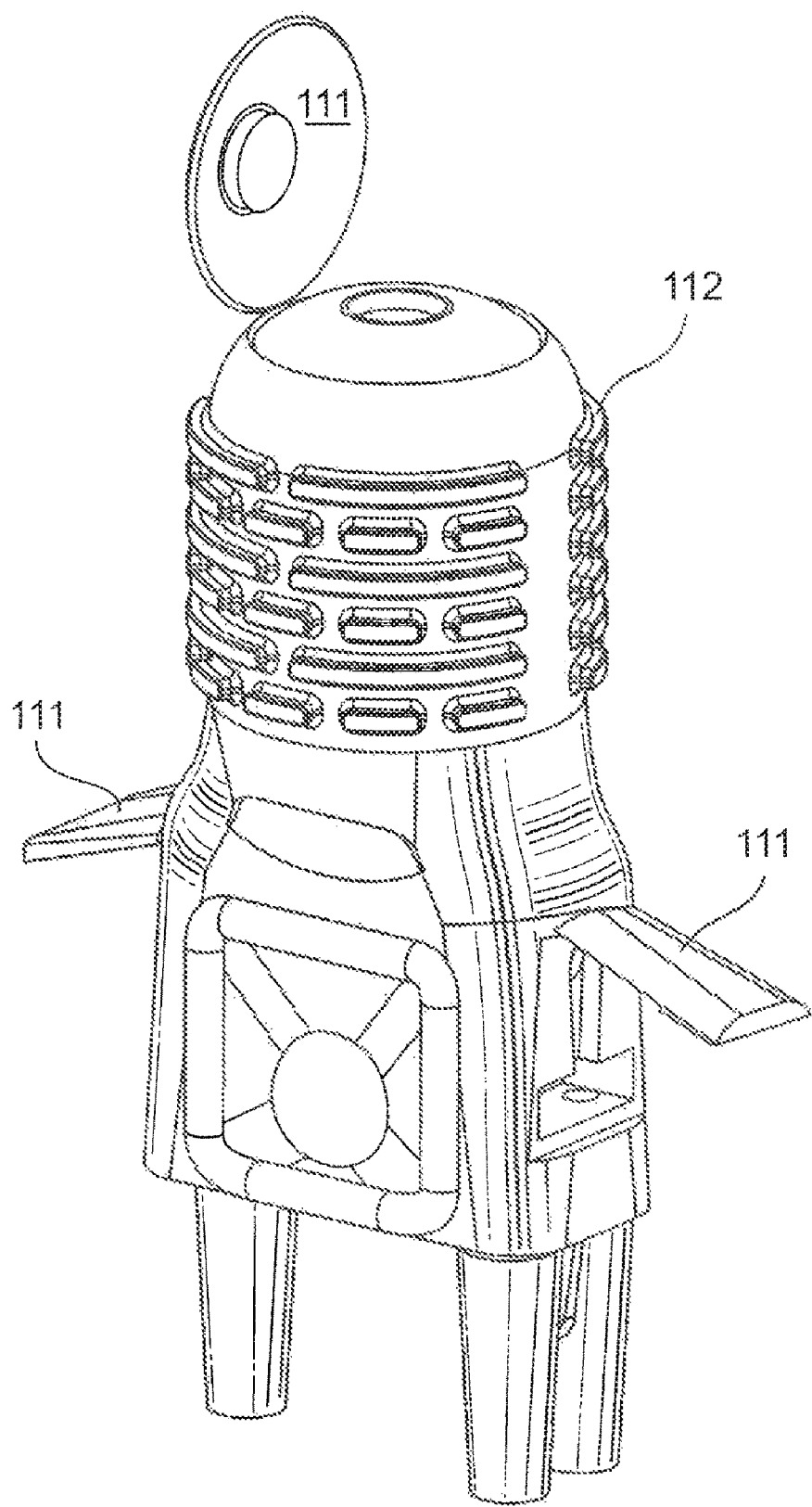
FIG. 39 is another perspective view of the housing of FIG. 36.
Figure 40:
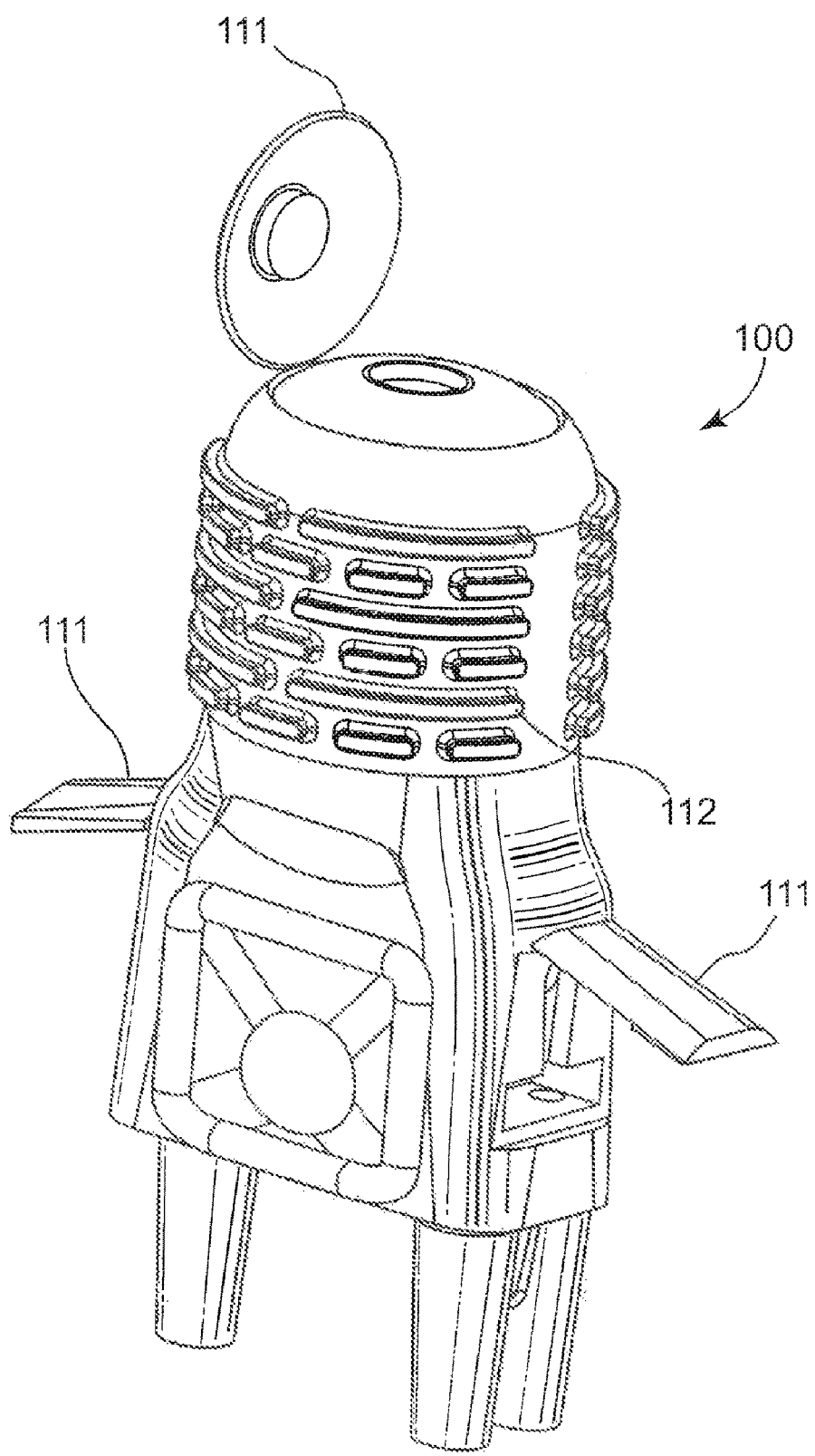
FIG. 40 is another perspective view of the housing of FIG. 36.

FIG. 35 is a sectional view of another embodiment. In this figure, the sphere 99A is shown in a deflate/lockout position with dashed lines and an active (pumping) position with solid lanes.

Referring now to FIGS. 36-40, there is shown another embodiment of housing 100 according to the present invention. The housing 100 includes protrusions 112. The housing 100 is particularly suitable for incorporating valve assemblies similar to those described with reference to FIGS. 31-35.

The housing 100 may advantageously be molded as a one-piece (e.g. integral or monolithic) part. To this end, the housing 100 preferably includes live hinges 111 that may be incorporated into the design/mold. Medical grade adhesives may be used to hold the live hinges in a closed or sealed position.

Various embodiments have been shown and describe protrusions and grooves. It is to be understood that though these embodiments have been shown and described in isolation, various features of each embodiment can be combined with the others to produce a variety of embodiments.

All patents, patent applications and journal articles cited herein are expressly incorporated by reference in their entirety.

While the present invention has been described with respect to a pump and valve assembly for a penile implant, the use of the present invention has many other applications within the scope and spirit of the present invention. For example, artificial sphincters utilize fluid pressure to maintain a body cavity or natural passageway in a closed or sealed state. When actuated, fluid pressure is released from the sphincter, causing the bodies' passageway to open. As such, the present invention may be utilized with an artificial sphincter as well.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited in the particular embodiments which have been described in detail therein. Rather, reference should be made to the appended claims as indicative of the scope and content of the present invention.

What is claimed is:

1. An implantable penile prosthesis comprising:
a reservoir, wherein said reservoir stores fluid;
a pump assembly, wherein said pump assembly is in fluid communication with the reservoir;
a cylinder in fluid communication with the pump assembly;
wherein said pump assembly includes a compressible bulb and a valve, wherein said valve includes a movable element that is positionable between a first position in a first flow path and a second position in a second flow path, the valve being changeable from a first configuration with the movable element in the first position with the second flow path open by compression of said compressible bulb so that a fluid pressure is generated within said pump assembly to act on said movable element to change the movable element from the first position to the second position and thus the valve from the first configuration to a second configuration with the first flow path open and the second flow path closed so as to permit valve operation to inflate said cylinder.

2. The implantable penile prosthesis of claim 1 further comprising a flexible housing within which the first and second flow paths are provided along with the first and second positions of the movable element, the housing also comprising an auto-deflate protrusion so that by compression of the housing at the auto-deflate protrusion, the movable element of the valve can be caused to move from the second position to the first position to open the second flow path and close the first flow path so as to permit valve operation to deflate said cylinder.

3. The implantable prosthesis of claim 1, wherein said movable element is moved between the first and second positions by way of a deformable portion of said pump assembly.

* * * * *